(12) United States Patent
Gutterman

(10) Patent No.: US 7,780,974 B2
(45) Date of Patent: Aug. 24, 2010

(54) AVICIN COATED STENTS

(75) Inventor: Jordan U. Gutterman, Houston, TX (US)

(73) Assignee: Research Development Foundation, Carson City, NV (US)

(*) Notice: Subject to any disclaimer, the term of this patent is extended or adjusted under 35 U.S.C. 154(b) by 1373 days.

(21) Appl. No.: 11/230,589

(22) Filed: Sep. 20, 2005

(65) Prior Publication Data
US 2006/0099236 A1 May 11, 2006

Related U.S. Application Data

(60) Provisional application No. 60/611,871, filed on Sep. 20, 2004.

(51) Int. Cl.
*A61F 2/06* (2006.01)
(52) U.S. Cl. ........................ 424/423; 623/1.15
(58) Field of Classification Search ................ None
See application file for complete search history.

(56) References Cited

U.S. PATENT DOCUMENTS

| 6,444,233 | B1 * | 9/2002 | Arntzen et al. | 424/725 |
| 6,746,696 | B2 * | 6/2004 | Arntzen et al. | 424/757 |
| 6,962,720 | B2 * | 11/2005 | Haridas et al. | 424/757 |
| 7,105,186 | B2 * | 9/2006 | Arntzen et al. | 424/757 |

| 2003/0031738 | A1 | 2/2003 | Haridas et al. |

FOREIGN PATENT DOCUMENTS

| WO | 00/10552 | 3/2000 |
| WO | 2004/012676 | 2/2004 |
| WO | WO-2004/026357 | 4/2004 |

OTHER PUBLICATIONS

Axel et al., "Paclitaxel Inhibits Arterial Smooth Muscle Cell Proliferation and Migration In Vitro and In Vivo Using Local Drug Delivery," *Circulation*, 96: 636-645, 1997.
Bhatia et al., "Drug-Eluting Intra-Coronary Stents: Have We Got the Magic Bullet?" *J. Postgrad. Med.*, 49: 291-296, 2003.
Casani et al., "Moderate Daily Intake of Red Wine Inhibits Mural Thrombosis and Monocyte Tissue Factor Expression in an Experimental Porcine Model," *Circulation*, 110: 460-465, 2004.
Drachman et al., "Neointimal Thickening After Stent Delivery of Paclitaxel: Change in Composition and Arrest of Growth Over Six Months," *J. American College of Cardiology*, 36(7): 2325-32, 2000.
Faxon et al., "Bringing Reality to Drug-Eluting Stents," *Circulation*, 109: 140-142, 2004.

(Continued)

*Primary Examiner*—Carlos A Azpuru
(74) *Attorney, Agent, or Firm*—Fulbright & Jaworski LLP

(57) ABSTRACT

The invention provides novel compositions and methods related to stents, such as coronary stents, comprising avicins, which are triterpene saponin compositions. In particular aspects of the invention, the avicins have growth-inhibiting properties and/or anti-inflammatory properties. In specific embodiments of the invention, the stent comprising the avicin reduces at least in part restenosis, such as that associated with stent procedures.

30 Claims, 5 Drawing Sheets

OTHER PUBLICATIONS

Gallo et al., "Inhibition of Intimal Thickening After Balloon Angioplasty in Porcine Coronary Arteries by Targeting Regulators of the Cell Cycle," *Circulation*, 99: 2164-2170, 1999.

Hanausek et al., "Avicins, a family of triterpenoid saponins from *Acacia victoriae* (Bentham), suppress H-*ras* mutations and aneuploidy in a murine skin carcinogenesis model," *PNAS*, 98(20): 11551-11556, 2001.

Haridas et al., "Avicins, a family of triterpenoid saponins from *Acacia victoriae* (Bentham), inhibit activation of nuclear factor κB by inhibiting both its nuclear localization and ability to bind DNA," *PNAS*, 98(20): 11557-11562, 2001.

Haridas et al., "Avicins: Triterpenoid saponins from *Acacia victoriae* (Bentham) induce apoptosis by mitochondrial perturbation," *PNAS*, 98(10): 5821-5826, 2001.

Haridas et al., "Triterpenoid electrophiles (avicins) activate the innate stress response by redox regulation of a gene battery," *J. Clin. Invest.*, 113: 65-73, 2004.

Heller, Letter to the editor, *Circulation*, 97(16): 1651, 1998.

Jayaraman et al., "Rapamycin-FKBP12 Blocks Proliferation, Induces Differentiation, and Inhibits cdc2 Kinase Activity in a Myogenic Cell Line," *J. Biol. Chem.*, 268(34): 25385-25388, 1993.

Jayatilake et al., "Isolation and Structures of Avicins D and G: In Vitro Tumor-Inhibitory Saponins Derived from *Acacia victoriae*," *J. Nat. Prod.*, 66: 779-783, 2003.

Joshi et al., "Metabolomics of Plant Saponins: Bioprospecting Triterpene Glycoside Diversity with Respect to Mammalian Cell Targets," *OMICS A Journal of Integrative Biology*, 6(3): 235-246, 2002.

Kim et al., "Novel Oral Formulation of Paclitaxel Inhibits Neointimal Hyperplasia in a Rat Carotid Artery Injury Model," *Circulation*, 109: 1558-1563, 2004.

Lanza et al., "Targeted Antiproliferative Drug Delivery to Vascular Smooth Muscle Cells With a Magnetic Resonance Imaging Nanparticle Contrast Agent," *Circulation*, 206: 2842-2847, 2002.

Laroia et al., "Drug-Eluting Stents," *Cardiology in Review*, 12: 37-43, 2004.

Lau et al., "Clinical impact of stent construction and design in percutaneous coronary intervention," *Am Heart J.*, 147: 764-73, 2004.

Lee, "'Me-Too' Products—Friend or Foe?" *N. Engl. J. Med.*, 350(3): 211-212, 2004.

Leon et al., "Drug-eluting stents and glycoprotein IIb/IIIa inhibitors: Combination therapy for the future," *Am. Heart J.*, 146: S13-7, 2003.

Luo et al., "Rapamycin Resistance Tied to Defective Regulation of p27$^{Kip1}$," *Mol. Cell. Biol.*, 16(12): 6744-6751, 1996.

Marks, "Cellular Functions of Immunophilins," *Physiological Reviews*, 76(3): 631-649, 1996.

Marx et al., "Rapamycin-FKBP Inhibits Cell Cycle Regulators of Proliferation in Vascular Smooth Muscle Cells," *Circulation Research*, 76: 412-417, 1995.

Moses et al., "Perspectives of Drug-Eluting Stents," *Am. J. Cardiovasc. Drugs*, 2(3): 163-172, 2002.

Mujoo et al., "Triterpenoid Saponins from *Acacia victoriae* (Bentham) Decrease Tumor Cell Proliferation and Induce Apoptosis," *Cancer Res.*, 61: 5486-5490, 2001.

Poon et al., "Rapamycin Inhibits Vascular Smooth Muscle Cell Migration," *J. Clin. Invest.*, 98(10): 2277-2283, 1996.

Salu et al., "Drug-eluting stents: a new treatment in the prevention of restenosis: Part I: experimental studies," *Acta Cardiol.* 59(1): 51-61, 2004.

Salu et al., "Drug-eluting stents: a new treatment in the prevention of restenosis: Part II: clinical studies," *Acta Cardiol.*, 59(2): 165-177, 2004.

Sawhney et al., "Treatment of Left Anterior Descending Coronary Artery Disease With Sirolimus-Eluting Stents," *Circulation*, 110: 374-379, 2004.

Schwertz et al., "Drug-Eluting Stents To Prevent Reblockage of Coronary Arteries," *J. Cardiovascular Nursing*, 18(1): 11-16, 2003.

Sindermann et al., "Paclitaxel and cyclosporine A show supra-additive antiproliferative effects on smooth muscle cells by activation of protein kinase C," *Basic Res. Cardiol.*, 97: 125-131, 2002.

Smith et al., "Antiproliferative Coatings for the Treatment of Coronary Heart Disease: What Are the Targets and Which Are the tools?" *J. Interven. Cardiol.*, 16: 475-483, 2003.

Stone et al., "A Polymer-Based, Paclitaxel-Eluting Stent in Patients with Coronary Artery Disease," *N. Engl. J. Med.*, 350: 221-31, 2004.

Sun et al., "Role for p27$^{Kip1}$ in Vascular Smooth Muscle Cell Migration," *Circulation*, 103: 2967-2972, 2001.

Woods et al., "Drug-Eluting Stents," *Annu. Rev. Med.*, 55: 169-78, 2004.

Yang et al., "Celecoxib, a Cycloxygenase-2 Inhibitor, Reduces Neointimal Hyperplasia Through Inhibition of Akt Signaling," *Circulation*, 110: 301-308, 2004.

\* cited by examiner

AVICIN COATED STENTS

The present invention claims priority to U.S. Provisional Patent Application Ser. No. 60/611,871, filed Sep. 20, 2004, which is incorporated by reference herein in its entirety.

BACKGROUND OF THE INVENTION

1. Field of the Invention

The present invention relates generally to at least the field of medicine. More specifically, it relates to compositions and methods regarding triterpene-coated stents.

2. Description of Related Art

One of the leading causes of death in the developed world is coronary artery disease. Intravascular therapy has emerged as a frequent practice in lieu of surgical intervention. Non-surgical treatments include balloon angioplasty and the use of coronary artery stents. Whereas the incidence of restenosis after angioplasty approached 50%, the use of stents reduced the incidence to about 30% at six months.

A major recent advance, the introduction of drug-coated stents for local drug delivery, has been revolutionary, reducing the incidence of in-stent restenosis to 3-5%. In-stent restenosis is due at least in part to intimal hyperplasia resulting from vascular smooth muscle cell growth and migration. Shortly after deflation of the balloon during angioplasty, the coronary artery undergoes "elastic recoil" and initiates a clot formation. Initially, platelets are activated, leading to formation of thrombi. Injury to the vessel wall causes release of cytokines and growth factors that recruit inflammatory cells and stimulate the growth and migration of smooth muscle cells. A chronic inflammatory process is thus started. The use of anti-thrombotic, anti-inflammatory and growth-inhibiting drugs have been used to prevent restenosis.

The most active coated stents to date are two natural anti-cancer drugs, both of which possess immunosuppressive, anti-inflammatory, and growth-inhibiting (of smooth muscle cells) properties—Rapamycin (Johnson & Johnson; New Brunswick, N.J.) and Taxol (Boston Scientific; Natick, Mass.). Particular examples of coatings that have been described include WO 2004/012676, which describes a medical device having a bioactive agent crosslinked with a crosslinking agent, such as genipin. In a specific embodiment, the bioactive agent is a flavone/terpene lactone. Additionally, WO 00/10552 describes anti-angiogenic substances utilized as a stent coating, wherein the substance may be triterpene acids.

While the studies to date have furthered the use of stents in treatment of coronary artery disease, there is still a great need in the art for alternative reagents for coated stents having new therapeutic benefits.

SUMMARY OF THE INVENTION

The present invention regards stents comprising a saponin composition including a triterpene or other aromatic terpenoid composition. Such a stent may be defined as "coated" with one or more active compound(s) as described herein. Those of skill in the art will understand that "coated" specifically encompasses any manner in which a given compound or collection of compounds can be associated with a stent, including permanent or non-permanent attachment to the surface of a stent, impregnation of a stent with the compound, encapsulation of a compound within the stent, local delivery of the compound with the stent, or any combinations thereof or other methods in which the compound is delivered in connection with the stent to obtain the associated benefits.

The saponins provided for producing coated stents may also comprise a glycosidic group. In a particular embodiment of the invention, there is provided a stent including triterpene saponins (called avicins), originally identified from the *Acacia victoriae* plant. In one embodiment, the present invention provides saponin compounds and mixtures thereof that may be isolated from the species *Acacia victoriae* and delivered in association with a stent. The use of any stent may benefit from comprising an avicin, including, for example, stents for arteriovenous fistula (a procedure that creates access to the blood for hemodialysis); reattaching the intestines after a temporary colostomy; and keeping the ureters open after surgery to repair a blocked ureter. In particular embodiments of the invention the stent is one to facilitate and maintain opening of a vessel, such as a coronary vessel, and this example is illustrated herein as an exemplary embodiment.

Avicins have a variety of properties indicating their efficacy in coating stents in accordance with the invention, including in particular general anti-inflammatory and anti-stress activities. Among specific characteristics are selective cytotoxic activity, the ability to release cytochrome c from mitochondria, induction of caspase activation and/or cleavage of PARP, inhibition of PI3-kinase and/or phosphorylation of Akt, induction of Rb gene hypophosphorylation, inhibition of carcinogenesis, inhibition of NF-κB activation, and/or inhibition of activators of cellular stress responses such as inducible nitric oxide synthase (NOS) and cyclooxygenase (COX-2).

In specific embodiments, avicins may be used in connection with stents for the prevention and/or therapy of restenosis. In specific embodiments of the present invention, avicins may be used in connection with stents to block platelet aggregation and/or thrombosis formation, for example, since both processes are a part of the primitive innate immune response. In further specific embodiments, the lipophilic properties of avicin provide an advantage, given the lipid solubility of the drug on the stents, making it particularly well-suited for sustained delivery from stents and prolonged deposition in blood vessels.

Avicins comprise potent anti-inflammatory effects, such as by their ability to inhibit activation of nuclear factor-κB (NF-κB) (a central regulator of an organism's response to stress signals) as well as its downstream targets of inducible nitric oxide synthase (iNOS) and cyclooxygenase (COX-2) (Haridas et al., 2001a). Inflammation and oxidative stress have been linked (Frenkel et al., 1995; Marnett, 2000), and the production of reactive oxygen species (ROS) provides a frequent source of endogenous genotoxins (Lengauer et al., 1998). Thus, in specific embodiments of the present invention, avicins reduce cell damage by minimization of physiological stress, such as that associated with stent implantation.

NF-κB regulates the transcription of a number of genes related to immune and inflammatory pathways, including proinflammatory cytokines, adhesion molecules, and apoptosis. Avicins may therefore find use in minimizing acute inflammation, as well as reducing both oxidative and nitrosative cellular stress to suppress undesirable cell proliferation. In specific embodiments of the present invention, avicins inhibit formation of neointima, which involves the recruitment of inflammatory cells to the stent "injury" site, the migration of VSMC from the media to the intima, and their cellular proliferation. In particular embodiments, avicins target one or more of these steps toward formation of neointima.

The avicins utilized on the stents for the present invention may comprise any formulation of avicins, but in specific embodiments may comprise Avicin D, Avicin G, Avicin B, and mixtures thereof. As indicated, avicins are considered saponin compounds, generally comprising a triterpene moiety, which is typically an acacic or oleanolic acid or other structurally similar triterpenoid moiety. The triterpene or triterpene glycoside compositions may also comprise a monoterpene moiety or moieties, and one of skill in the art will appreciate that the saponin compositions may be further substituted with other chemical functionalities. Thus, the saponin compounds may comprise a triterpene moiety attached to at least one, and preferably two, three, or more, monoterpene moieties. When more than one monoterpene moiety is present, these moieties may each be attached (i) directly to the triterpene moiety; (ii) to a sugar, or other linking group, which is attached to the triterpene moiety; and/or (iii) to a monoterpene moiety which is attached to the triterpene moiety directly or through a sugar or other linking groups. Exemplary linking groups include sugars, acyl, amide, alkoxy, ketyl, alkyl, alkylene and other similar chemical moieties including those that would be apparent to one of skill in the art. The triterpene glycosides of the invention typically have a molecular weight in the range of 1800 to 2600 amu, or from at least 1800, 1900, 2000, 2100 amu to about 2200, 2300, 2400 or 2600 amu, for example.

An important aspect of the invention provides the use of a stent comprising a mixture comprising one or more isolated saponins or triterpene glycosides that may be characterized as isolatable from the tissues of *Acacia victoriae*. Such a compound may be defined as having a biological activity comprising induction of cytotoxicity in a Jurkat cell with an $IC_{50}$ of from about 0.12 to about 0.40 µg/ml. In other embodiments of the invention, the apoptosis may be induced when administered to a Jurkat cell at a concentration of from about 100 to about 400 ng/ml. The activity may in certain embodiments be further defined as the ability to activate caspase-3 in a Jurkat cell, wherein the caspase activity is in the range of from about 0.3 to about 1.6 fluorescence units/minutes/mg; and may still further be defined as the ability to cause the cleavage of PARP in a Jurkat cell.

In certain aspects of the invention, a method is provided of preventing the abnormal proliferation of mammalian epithelial cells in a mammal comprising administering to the mammal a stent comprising a therapeutically effective amount of the avicin compositions described herein. There is also provided a method of locally treating and/or preventing inflammation in a mammal, comprising administering to the mammal a stent comprising a therapeutically effective amount of the compositions described herein. Another important aspect of this invention is a method of regulating angiogenesis in a mammal comprising administering to the mammal a therapeutically effective amount of a stent comprising the pharmaceutical compositions described. In a related embodiment of the invention, the mammal is a human.

The compositions for coating a stent may comprise a purified triterpene compound comprising a triterpene moiety attached to a monoterpene moiety having the molecular formula:

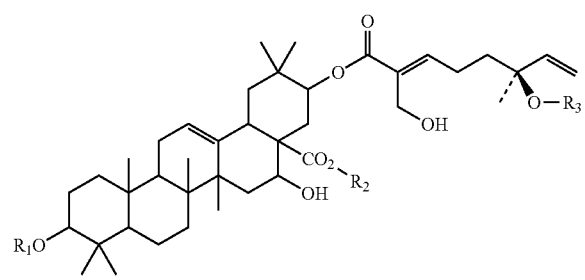

or a pharmaceutical formulation thereof, wherein a) $R_1$ and $R_2$ are selected from the group consisting of hydrogen, C1-C5 alkyl, and an oligosaccharide; b) $R_3$ is selected from the group consisting of hydrogen, hydroxyl, C1-C5 alkyl, C1-C5 alkylene, C1-C5 alkyl carbonyl, a sugar, and a monoterpene group; and c) the formula further comprises $R_4$, wherein $R_4$ is selected from the group consisting of hydrogen, hydroxyl, C1-C5 alkyl, C1-C5 alkylene, C1-C5 alkyl carbonyl, a sugar, C1-C5 alkyl ester, and a monoterpene group, and wherein $R_4$ may be attached to the triterpene moiety or the monoterpene moiety. The invention also contemplates the compound wherein $R_3$ is a sugar. In related embodiments of the invention, the sugar is selected from the group consisting of glucose, fucose, rhamnose, arabinose, xylose, quinovose, maltose, glucuronic acid, ribose, N-acetyl glucosamine, and galactose. In other related embodiments of the invention, the compound further comprises a monoterpene moiety attached to the sugar. The invention also comprises a composition wherein $R_3$ has the following formula

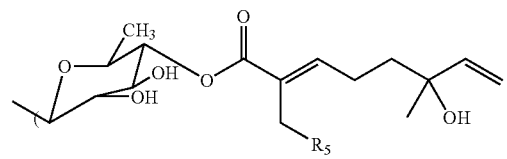

wherein R5 is selected from the group consisting of hydrogen, hydroxyl, C1-C5 alkyl, C1-C5 alkylene, C1-C5 alkyl carbonyl, a sugar, C1-C5 alkyl ester, and a monoterpene group.

In one embodiment of the invention, $R_5$ is a hydrogen or a hydroxyl. In another embodiment of the invention, $R_1$ and $R_2$ each comprise an oligosaccharide. In still other embodiments of the invention, $R_1$ and $R_2$ each comprise a monosaccharide, a disaccharide, a trisaccharide or a tetrasaccharide. In related embodiments of the invention $R_1$ and $R_2$ each comprise an oligosaccharide comprising sugars which are separately and independently selected from the group consisting of glucose, fucose, rhamnose, arabinose, xylose, quinovose, maltose, glucuronic acid, ribose, N-acetyl glucosamine, and galactose. In further aspects of the invention, at least one sugar is methylated.

In one embodiment of the invention, $R_4$ is attached to the triterpene moiety through one of the methylene carbons attached to the triterpene moiety. In another embodiment of the invention, the triterpene moiety is oleanolic acid instead of acacic acid.

Another embodiment of the invention utilizes a composition comprising a triterpene glycoside having the molecular formula:

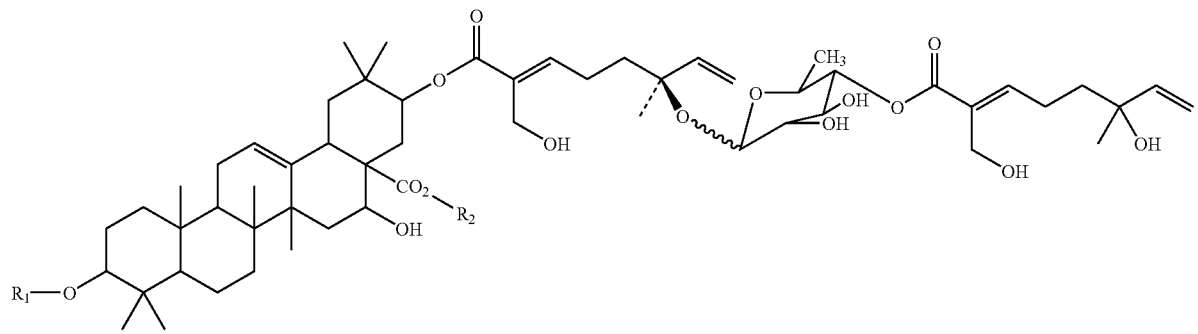

or a pharmaceutical formulation thereof, wherein a) $R_1$ is an oligosaccharide comprising N-acetyl glucosamine, fucose and xylose; and/or b) $R_2$ is an oligosaccharide comprising glucose, arabinose and rhamnose. In a related embodiment the compound having the molecular formula:

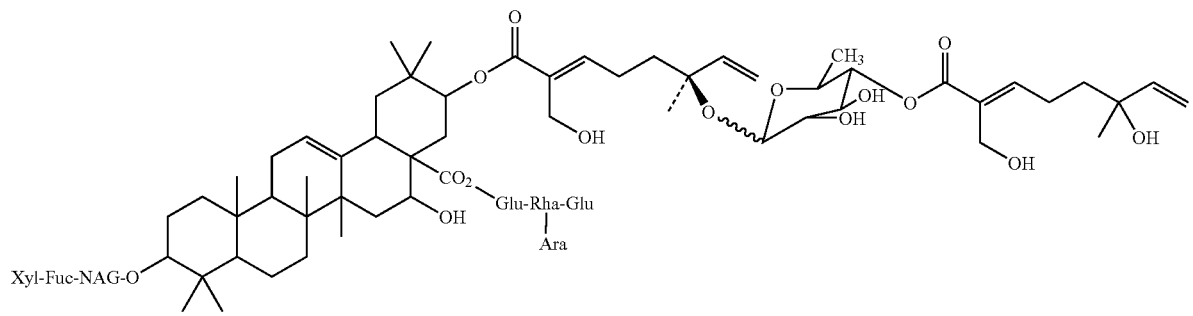

or a pharmaceutical formulation thereof is utilized for the stent.

Another aspect of the invention utilizes a composition comprising a triterpene glycoside having the molecular formula:

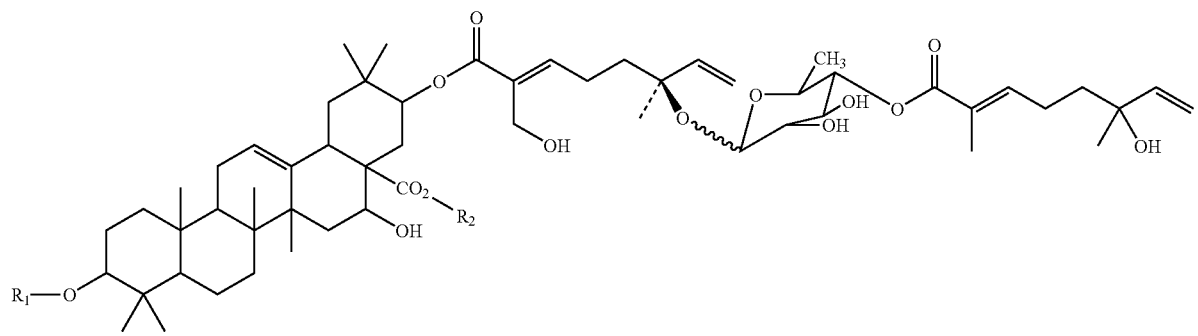

or a pharmaceutical formulation thereof wherein, a) $R_1$ is an oligosaccharide comprising N-acetyl glucosamine, fucose and xylose; and/or b) $R_2$ is an oligosaccharide comprising glucose, arabinose and rhamnose. A related aspect of the invention utilizes a composition having the molecular formula:

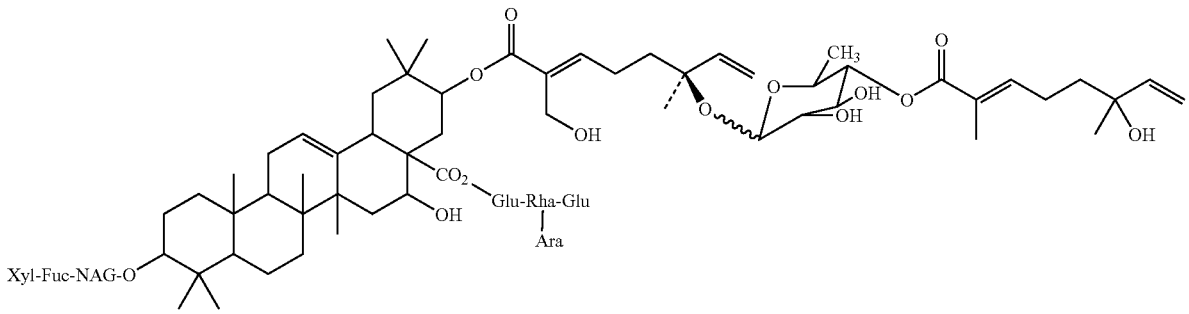

or a pharmaceutical formulation thereof.

Yet another aspect of the invention employs a composition comprising a triterpene glycoside having the molecular formula:

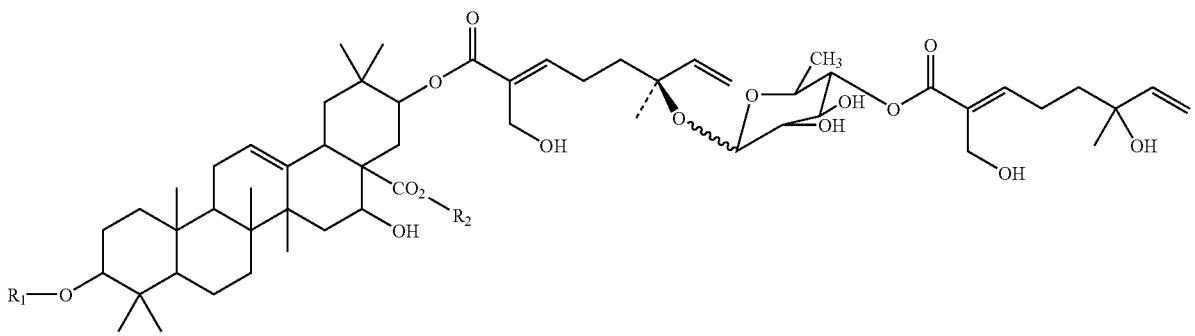

or a pharmaceutical formulation thereof, wherein, a) $R_1$ is an oligosaccharide comprising N-acetyl glucosamine, glucose, fucose and xylose; and/or b) $R_2$ is an oligosaccharide comprising glucose, arabinose and rhamnose. A related aspect of the invention employs a composition comprising having the molecular formula:

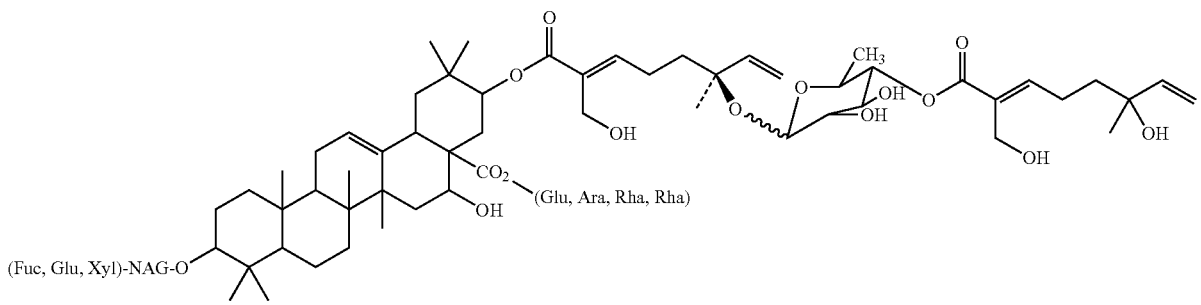

The triterpene moiety of the method can comprise the formula:

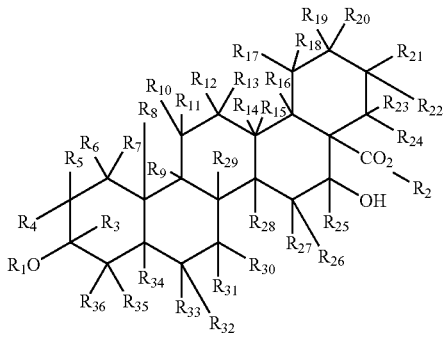

or may be an isomer thereof wherein, a) R1 and R2 are selected from the group consisting of hydrogen, C1-C5 alkyl, C1-C5 alkylene, C1-C5 alkyl carbonyl, a sugar, an oligosaccharide; b) wherein R3-R36 are each separately and independently selected from the group consisting of a point of unsaturation, hydrogen, hydroxyl, C1-C5 alkyl, C1-C5 alkylene, C1-C5 alkyl carbonyl, a sugar, C1-C5 alkyl ester, and a monoterpene group; and/or c) at least one of R3-R36 is a monoterpene group. The isomer can be an optical isomer, a stereoisomer or a cis isomer or a trans isomer.

In some embodiments, R1 and R2 each comprise an oligosaccharide. In some specific aspects of this embodiment, R1 and R2 each comprise a monosaccharide, a disaccharide, a trisaccharide or a tetrasaccharide. In other specific aspects of the method, R1 and R2 each comprise an oligosaccharide comprising sugars that are separately and independently selected from the group consisting of glucose, fucose, rhamnose, arabinose, xylose, quinovose, maltose, glucuronic acid, ribose, N-acetyl glucosamine, and galactose. In yet another specific aspect of the method, at least one sugar is methylated.

In other embodiments of the method, R4 is attached to the triterpene moiety through one of the methylene carbons attached to the triterpene moiety. In another aspect the triterpene moiety further comprises at least one double bond.

In yet other embodiments of the method, the triterpene moiety is an acacic acid ester, a oleanolic acid ester, a betulinic acid ester, an ursolic acid ester, a quinovic acid ester, a pomolic acid ester, a rotundic acid ester, a rotungenic acid ester, a madasiatic acid ester, an asiatic acid ester, an euscaphic acid ester, a tormentic acid ester, madecassic acid ester, a lupeolic acid ester, a cylicodiscic acid ester, a mollic acid ester, a jessic acid ester, an echinocystic acid ester, or an entagenic acid ester or other structurally similar triterpenoid moiety.

The monoterpene moiety of the composition used in the method comprises the formula:

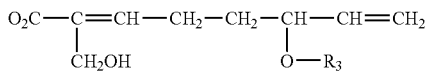

or is an isomer thereof wherein,
a) R3 is selected from the group consisting of hydrogen, hydroxyl, C1-C5 alkyl, C1-C5 alkylene, C1-C5 alkyl carbonyl, a sugar, and a monoterpene group; and/or
b) the formula further comprises R4, wherein R4 is selected from the group consisting of hydrogen, hydroxyl, C1-C5 alkyl, C1-C5 alkylene, C1-C5 alkyl carbonyl, a sugar, C1-C5 alkyl ester, and a monoterpene group.

The isomer maybe either a cis isomer or a trans isomer.

In other embodiments of the method, R3 is a sugar. The sugar is selected from the group consisting of glucose, fucose, rhamnose, arabinose, xylose, quinovose, maltose, glucuronic acid, ribose, N-acetyl glucosamine, and galactose. The composition of the method can further comprise another monoterpene moiety attached to the sugar.

In some specific embodiments of the method, the monoterpene composition comprises the formula:

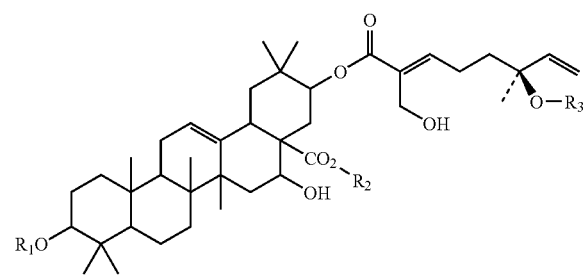

or an isomer thereof, wherein,
a) $R_1$ and $R_2$ are selected from the group consisting of hydrogen, C1-C5 alkyl, and an oligosaccharide;
b) $R_3$ is selected from the group consisting of hydrogen, hydroxyl, C1-C5 alkyl, C1-C5 alkylene, C1-C5 alkyl carbonyl, a sugar, and a monoterpene group; and/or
c) the formula further comprises $R_4$, wherein $R_4$ is selected from the group consisting of hydrogen, hydroxyl, C1-C5 alkyl, C1-C5 alkylene, C1-C5 alkyl carbonyl, a sugar, C1-C5 alkyl ester, and a monoterpene group, and wherein $R_4$ may be attached to the triterpene moiety or the monoterpene moiety.

The isomer is a stereoisomer or an optical isomer, in some embodiments.

In yet another specific embodiments, the monoterpene composition comprises the formula:

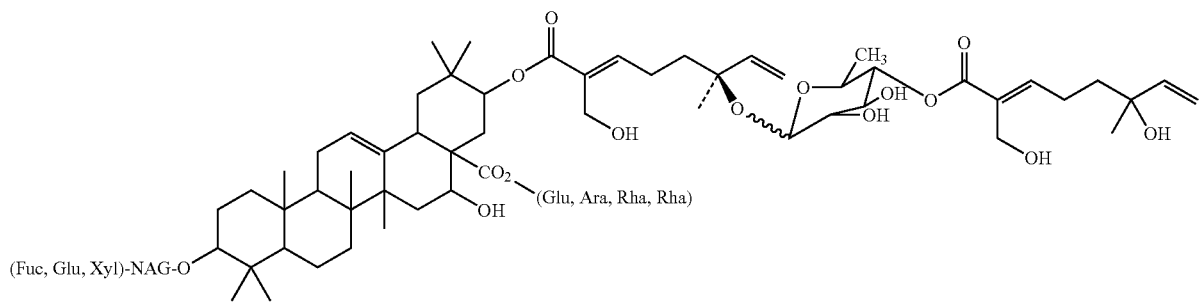

In other aspects of the method the inflammatory responses are inhibited when the monoterpene composition is administered to a cell at a concentration of from about 0.5 to about 2.0 μg/ml.

Another aspect of the invention relates to a stent comprising a composition including a triterpene moiety, an oligosaccharide and three monoterpene units. In one embodiment the triterpene moiety is acacic acid or oleanolic acid.

Although in a particular embodiment the invention relates to a stent comprising one or more avicins, in an alternative embodiment the avicin is administered systemically to an individual having the stent, either alone or in combination with the same or nonidentical avicin comprised on the stent.

Thus, an embodiment of the present invention is a stent comprising an avicin. Although any avicin is suitable, in specific embodiments the avicin is Avicin D, Avicin G, Avicin B, or a mixture thereof. The avicin may be further defined as a composition comprising a triterpene moiety attached to a monoterpene moiety having the molecular formula:

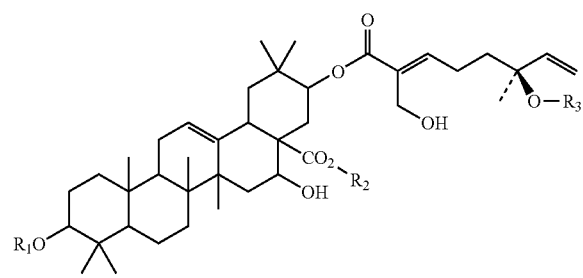

or a pharmaceutical formulation thereof, wherein a) R1 and R2 are selected from the group consisting of hydrogen, C1-C5 alkyl, and an oligosaccharide; b) R3 is selected from the group consisting of hydrogen, hydroxyl, C1-C5 alkyl, C1-C5 alkylene, C1-C5 alkyl carbonyl, a sugar, and a monoterpene group; and/or c) the formula further comprises R4, wherein R4 is selected from the group consisting of hydrogen, hydroxyl, C1-C5 alkyl, C1-C5 alkylene, C1-C5 alkyl carbonyl, a sugar, C1-C5 alkyl ester, and a monoterpene group, and wherein R4 may be attached to the triterpene moiety or the monoterpene moiety. In particular, R3 may be a sugar, such as one selected from the group consisting of glucose, fucose, rhamnose, arabinose, xylose, quinovose, maltose, glucuronic acid, ribose, N-acetyl glucosamine, and galactose. In specific embodiments, the avicin further comprises a monoterpene moiety attached to the sugar.

In additional embodiments, the stent of the present invention comprises an avicin wherein R3 has the following formula

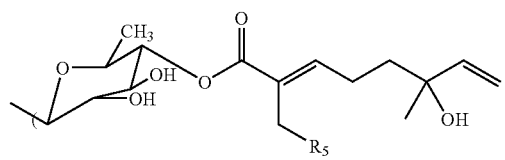

wherein R5 is selected from the group consisting of hydrogen, hydroxyl, C1-C5 alkyl, C1-C5 alkylene, C1-C5 alkyl carbonyl, a sugar, C1-C5 alkyl ester, and a monoterpene group. In particular embodiments, the R5 is a hydrogen or a hydroxyl. In other particular embodiments, the R1 and R2 each comprise an oligosaccharide, although in other embodiments each may comprise a monosaccharide, a disaccharide, a trisaccharide or a tetrasaccharide. In further specific embodiments, R1 and R2 each comprise an oligosaccharide comprising sugars that are separately and independently selected from the group consisting of glucose, fucose, rhamnose, arabinose, xylose, quinovose, maltose, glucuronic acid, ribose, N-acetyl glucosamine, and galactose. In specific embodiments, at least one sugar is methylated. The R4 may be attached to the triterpene moiety through one of the methylene carbons attached to the triterpene moiety, and in specific embodiments the triterpene moiety is oleanolic acid instead of acacic acid.

In particular embodiments of the invention, the stent includes an avicin composition further defined as comprising a triterpene glycoside having the molecular formula:

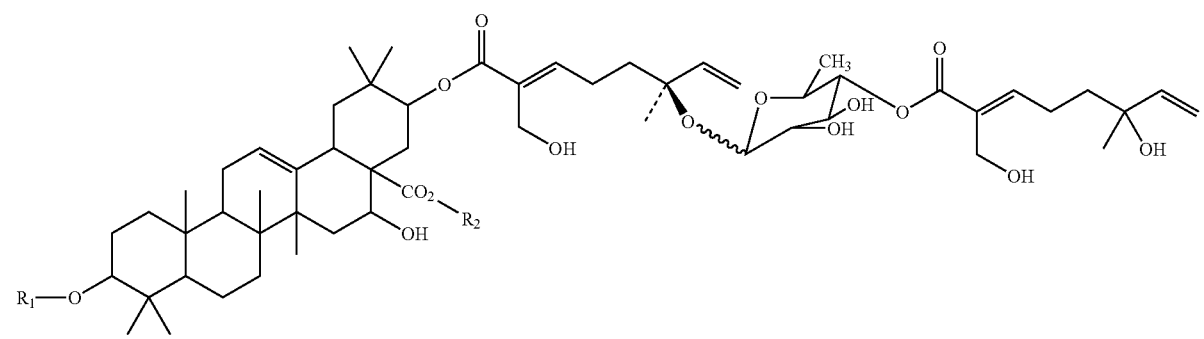

or a pharmaceutical formulation thereof, wherein a) R1 is an oligosaccharide comprising N-acetyl glucosamine, fucose and xylose; and/or b) R2 is an oligosaccharide comprising glucose, arabinose and rhamnose.

In other embodiments, the stent comprises an avicin having the molecular formula:

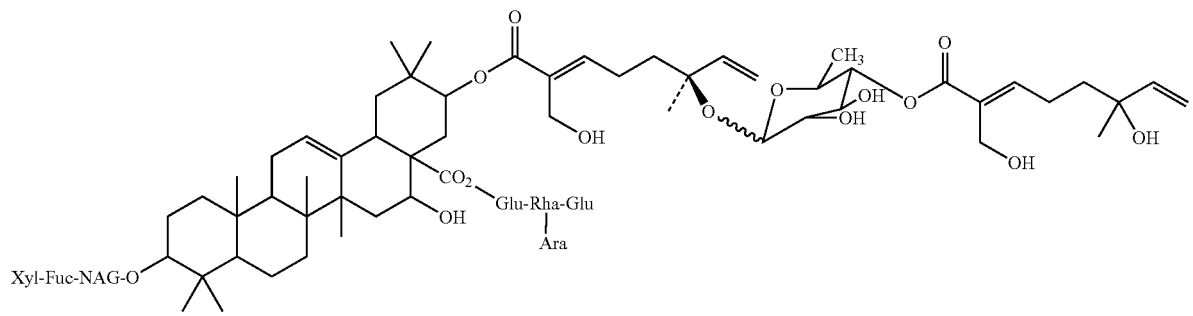

or a pharmaceutical formulation thereof.

In particular, the avicin on the stent is further defined as a triterpene glycoside having the molecular formula:

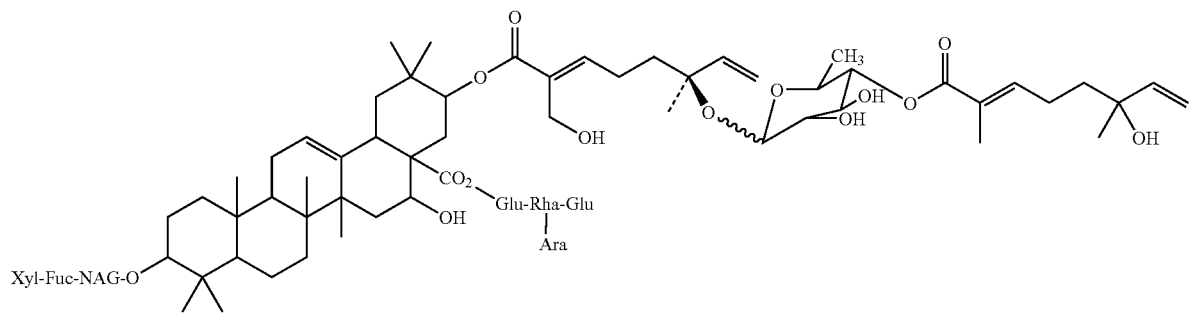

or a pharmaceutical formulation thereof wherein, a) R1 is an oligosaccharides comprising N-acetyl glucosamine, fucose and xylose; and/or b) R2 is an oligosaccharides comprising glucose, arabinose and rhamnose.

The avicin for the stent may have the molecular formula:

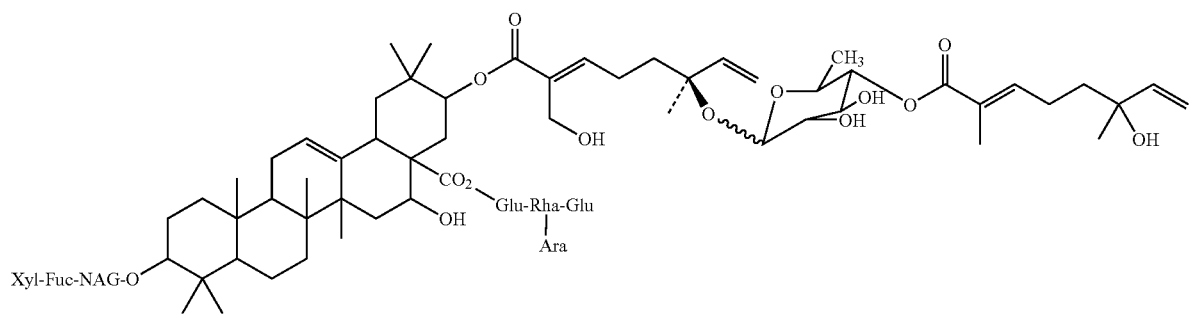

or a pharmaceutical formulation thereof. The avicin may be further defined as comprising a triterpene glycoside having the molecular formula:

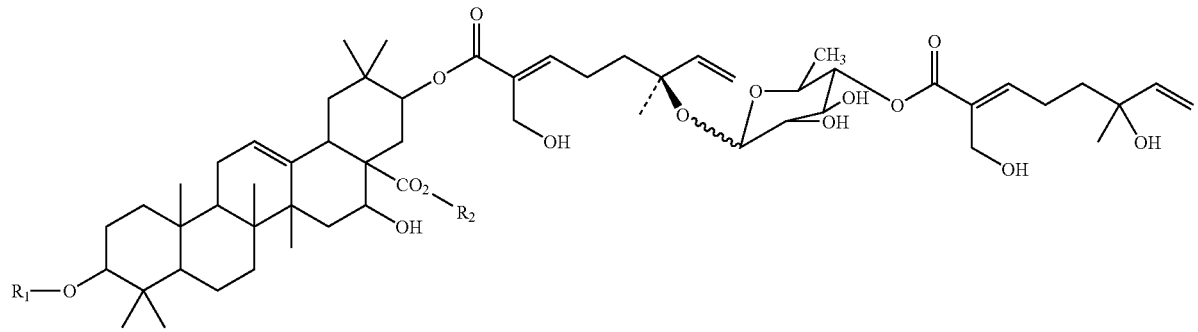

or a pharmaceutical formulation thereof, wherein, a) R1 is an oligosaccharide comprising N-acetyl glucosamine, glucose, fucose and xylose; and/or b) R2 is an oligosaccharide comprising glucose, arabinose and rhamnose. The avicin may be further defined as having the molecular formula:

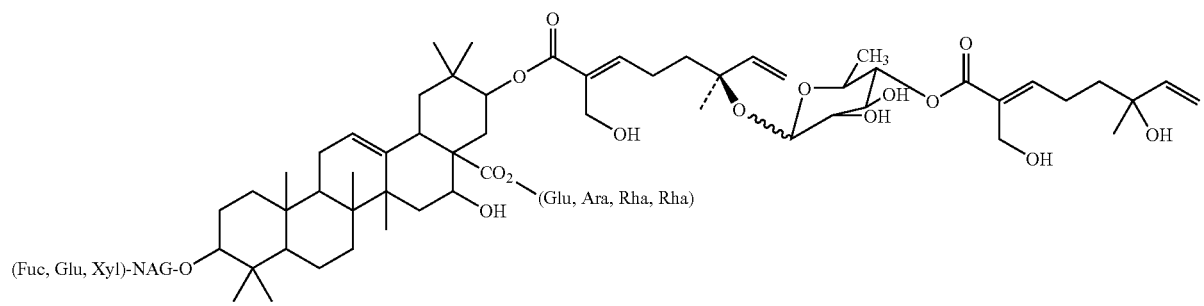

The avicin may be further defined as comprising a triterpene moiety, an oligosaccharide and three monoterpene units, and the triterpene moiety is acacic acid or oleanolic acid.

In particular embodiments of the present invention, the stent further comprising an additional compound selected from the group consisting of an immunosuppressing agent, an anti-clotting agent, an antibiotic, an anti-inflammatory agent and mixtures thereof. The additional compound may be coated on the stent.

The stent may comprise a corrugated configuration, slotted configuration, a coil configuration, a coil-related configuration, a tubular configuration, a multicellular configuration, or a combination thereof. The stent may be comprised of a metal, such as stainless steel, tantalum, nitinol, cobalt-chromium alloy; or a polymer, such as a biodegradable polymer, a synthetic polymer, or both. The biodegradable polymer may comprise phosphorylcholine or poly-L-lactic acid, for example. In particular, the stent may further comprise gold or silicon carbide.

In an additional embodiment of the present invention, there is a method of treating restenosis in an individual, comprising providing a stent; at least partially coating said stent with one or more avicin compounds; and delivering the stent comprising the avicin to the individual. In specific embodiments, the stent is fully coated by the avicin compound. In other embodiments, the avicin compound is elutable from the stent. In particular, the delivering step comprises delivering the stent to an artery of the individual, which may be a coronary artery.

In a specific embodiment, the method further comprises the step of providing an additional therapy to the individual, such as a restenosis therapy. The additional restenosis therapy may comprise drug therapy, such as therapy with an anti-clotting agent, an anti-inflammatory agent, or a mixture thereof. In another embodiment, the additional therapy comprises a coronary artery disease therapy, such as surgery, drug therapy, diet changes, and/or exercise changes, for example. The additional therapy may be both an additional restenosis therapy and an additional coronary artery disease therapy.

In additional embodiments of the present invention, there is a method of treating restenosis in an individual comprising administering to the individual a stent comprising an avicin.

In another embodiment, there is a method of inhibiting the proliferation of an endothelial cell in a mammal comprising administering to said mammal a stent comprising an avicin. The endothelial cell may be further defined as a smooth muscle cell, and the mammal may be a human.

In an additional embodiment, there is a method of inducing apoptosis in an endothelial cell of a mammal comprising administering to the mammal a therapeutically effective amount a stent comprising an avicin. The endothelial cell may be further defined as a smooth muscle cell. In another embodiment, there is a method of treating a mammal for inflammation comprising administering to said mammal a therapeutically effective amount of a stent comprising an avicin.

In another embodiment of the present invention, there is a method of manufacturing a stent comprising coating the stent with an avicin. The method may be further defined as comprising providing a stent; providing at least one avicin; and applying said avicin to the stent. The applying step may be further defined as dipping at least part of the stent in a composition comprising the avicin. The applying step may be further defined as spraying at least part of the stent with a composition comprising the avicin. In a specific embodiment, the method further comprises the step of drying the avicin onto the stent.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
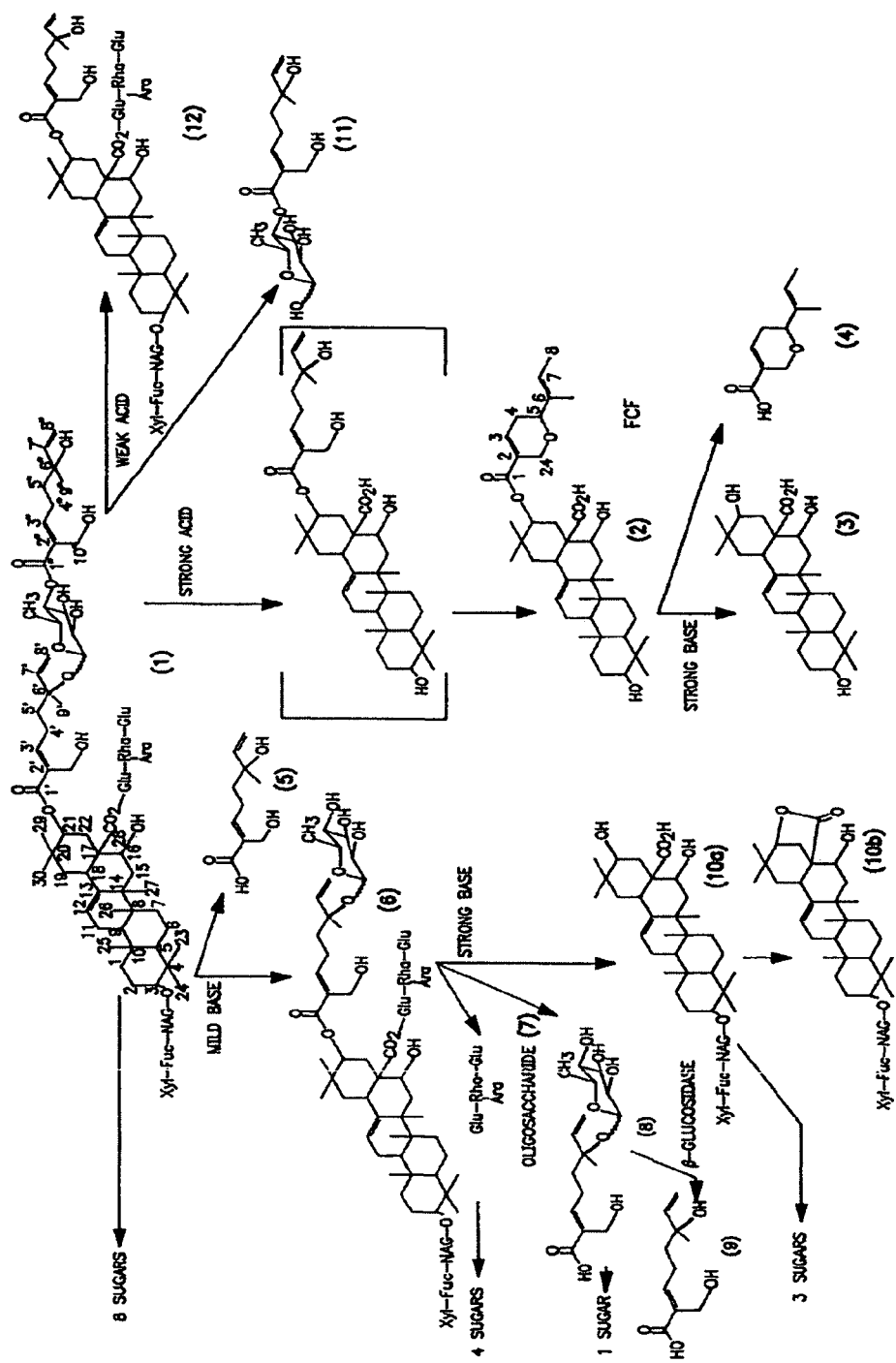
FIG. 1: Depicts compounds from the degradation of compound D1.

As used herein "another" may mean at least a second or more. In certain aspects, one or more compositions and/or methods of the invention may consist of or consist essentially of one or more embodiments. Also, one of skill in the art recognizes that a particular embodiment of the invention is exemplary in nature and will apply to other embodiments of the invention.

The invention seeks to overcome limitations in the prior art by providing stents comprising novel biologically active triterpene glycoside compositions. In particular, the present inventor has identified and purified triterpene compounds from *Acacia victoriae*, and their use is described to enhance utilization of a structural support for a vessel, such as an artery, while reducing the rate or occurrence of restenosis or preventing restenosis following placement of the structural support. The support may be further defined as a stent.

I. COMPOSITIONS OF THE PRESENT INVENTION

The compositions regard a stent comprising an avicin, exemplary embodiments of which are as follows.

A. Stents

A stent is referred to herein as a device that is inserted into a tubular structure, such as a blood vessel, to act as a structural scaffold for the tubular structure. A variety of therapeutic purposes utilize stents, including creating an arteriovenous fistula (a procedure that creates access to the blood for hemodialysis); reattaching the intestines after a temporary colostomy; and keeping the ureters open after surgery to repair a blocked ureter, although in particular embodiments of the invention the purpose is to facilitate and maintaining opening of a coronary vessel.

For the coronary stent embodiment, a stent is used to hold open an artery that has become too narrow, for example, due to atherosclerosis. In atherosclerosis, plaque builds up on the inner walls of arteries, the blood vessels that carry oxygen-rich blood throughout the body. As the artery walls thicken, the pathway for blood narrows, which can impede or block blood flow. In particular embodiments, a stent is used when the artery may have previously been cleared using angioplasty.

In particular embodiments, the stent may be of any suitable design. In specific embodiments, it is further described as a thread, rod, or catheter. In specific embodiments, the stent is a small, expandable slotted metal tube, which may be referred to as a wire mesh tube. In other embodiments, the stent may be any as reviewed in Lau et al. (2003), for example, wherein there is described a corrugated configuration, slotted configuration, coil configuration, coil-related configuration, tubular configuration, the multicellular configuration (which has the same support property as the slotted tube stent, but has fewer strut-strut intersections), and so forth. It is known that corrugated stents may be preferred over slotted stents, given that there is reduced vascular damage and reduced neointimal hyperplasia as a result of the corrugated design having fewer strut-strut intersections. It is also known that the stent configuration determines the luminal geometry, which thereby dictates the vascular response separate and apart from vascular injury. Specifically, a uniformly circular lumen shape having evenly spaced struts elicits less vessel wall reaction than a lumen having less of a circular design. In particular aspects, stents having low or lower metal density than others, such as by providing thinner struts or wider interfilament distances, and those having a lower crossing profile, are desirable, particularly for smaller vessels.

It is also known that there is a relationship between stent performance and strut thickness. Increasing strut thickness may improve immediate stent performance, which then increases at least radiovisibility, radial strength, and arterial wall support, although too much thickness of the struts results in vascular wounding and may trigger an increase in undesirable intimal hyperplasia.

In particular embodiments, the stent is configured such that it is employable for permanent use, for temporary use, or either permanent or temporary use.

The material of the stent may be of any suitable kind so long as it is compatible with the target tissue. Some desirable properties include inertness, resistance to corrosion, elasticity, and a high radial strength for favorable scaffolding support, to name an exemplary few. In specific embodiments, the material may comprise surgical grade 316L stainless steel, which has a high tensile strength, provides sufficient resistance to corrosion, and is nonferromagnetic. Sometimes, however, the stainless steel may elute a minimum amount of nickel, molybdenum, and chromium, which may trigger an immune and inflammatory response. Other suitable materials include tantalum, nitinol (an alloy of nickel and titanium), cobalt-chromium alloy, biodegradable polymers, such as phosphorylcholine and poly-L-lactic acid, and/or synthetic polymers may be utilized.

In addition to the avicins, the stent may be coated with one or more materials to improve functionality, biocompatibility, to improve the surface texture and roughness, and/or to localize drug delivery. Such materials to influence the surface properties of the stent include gold, silicon carbide, phosphorylcholine, heparin, antiproliferative drugs, such as rapamycin (also referred to as sirolimus) and Taxol (also referred to as paclitaxel).

In specific embodiments, the stents of the present invention are utilized not only to physically support the artery but as drug-delivery vehicles, such as to enhance the therapy for which the stent is being utilized. They are particularly suited to local administration of an effective amount of the avicin. That is, the avicin can be prolonged and intramurally deposited into the vessel wall at the precise location in a sufficient concentration, and at the time of and after vessel injury. These stents are sometimes referred to as a "coated" or "medicated" stent. That is, a drug-eluting stent is a normal metal stent that has been coated with a pharmacologic agent (drug) that is known to interfere with the process of restenosis (reblocking).

Thus, in specific embodiments of the present invention, there is a stent comprising at least one therapeutic composition, wherein at least one of the therapeutic compositions is an avicin. Additional compounds other than avicins for use on the stents of the invention include, for example, antithrombotic agents, such as heparin, GP IIb/IIIa inhibitors, and/or hirudin/iloprost; antiproliferative agents, such as corticoids, dexamethasone, sirolimus (rapamycin), paclitaxel (Taxol), tacrolimus, everolimus, ABT-578, 17-β-oestradiol, angiopeptin, mycophenolic acid, batimastat, actinomycin D, tyrosine kinase inhibitors (such as ST638), and actin-skeleton inhibitors; clot-deterring agents; radiation, such as gamma or beta radiation (brachytherapy); an immunosuppressant, such as a cyclosporin, azathioprine, or corticosteroid, for example; an antibiotic, such as gentamycin, tobramycin, amoxicillin, amphotericin B, ampicillin, azithromycin, cefazolin, cefepime, Cefotaxime, cefotetan, Ceftazidime Ceftizoxime Ceftriaxone Cefuroxime Chloramphenicol Ciprofloxacin Clindamycin, erythromycin, Fluconazole Gatifloxacin Imipenem, penicillin, Piperacillin, rifampin, Piperacillin, and/or vancomycin, for example; or a mixture thereof, and in specific embodiments the stents of the present invention further comprise one or more of these agents. Specific attributes to stents of the present invention may include the use of inorganic elements, such as gold, for example; polymers, such as polylactic acid and fibrin, for example; and immobilized drugs, such as heparin and abciximab (an antibody that targets glycoprotein IIb/IIIa (GP IIbIIIa) on platelets), for example.

In specific embodiments, the stent of the present invention is defined as a device for the controlled release of one or more avicins and comprises an implantable stent and, in further specific embodiments, a release system. The release system may be of any suitable kind, although in a particular embodiment the system comprises that of U.S. Pat. No. 6,656,162, such as wherein the release system comprises at least two reservoirs, wherein the system provides pulsatile release of the one or more drugs from the at least two reservoirs. In other embodiments, the at least two reservoirs are each covered by a reservoir cap, and the drug may be released from the reservoirs by passive means. In another embodiment, the reservoir cap is formed of a material that degrades or dissolves over time. In a further specific embodiment, the reservoir cap is formed of a non-degradable material that is permeable to the one or more drugs.

In some embodiments, in furtherance to methods and compositions described herein, there may be targeted paramagnetic nanoparticles comprising the avicin and/or an additional drug, wherein the nanoparticles are utilized as a MRI-visualizable and quantifiable drug delivery system (Lanza et al., 2002).

In specific embodiments, the release system comprises drug molecules in a matrix formed of a degradable material, such as a biodegradable polymer. The polymer may be naturally-occuring or synthetic, such as a polyamide, polyester, polyanhydride, polyorthoester, or polycarbonate. The release system may further comprise a bioerodible hydrogel, such as wherein the one or more drugs are in the form of a solid or gel. The release system may further comprise at least one excipient or diluent.

The stent may be structured by any suitable means, although in a specific embodiment is structured in accordance with U.S. Pat. No. 6,206,915, thereby comprising an outer member having a lumen; a cannulated inner member positioned within the lumen of the outer member; and a space separating the inner member from the outer member. The drug may be disposed within the space separating the inner member from the outer member, for example. There may also be a pattern of perforation extending from the outer member through the inner members, so as to permit the stent to expand in diameter. In specific embodiments, the inner and outer member are concentrically aligned. In one embodiment, there is a stent comprising first and second tubular members concentrically aligned about a longitudinal axis, and defining a substantially cylindrical profile; a space defined by an outer surface of the second tubular member and an inner surface of the first tubular member, wherein said space contains a therapeutic drug; and means for maintaining the space between the second member and the first member, said means also providing a friction fit between the second member and the first member.

In another embodiment of the present invention, there is a drug delivery stent assembly as described in U.S. Pat. No. 5,891,108 and includes a hollow tubular metal wire stent that extends in a path defining a generally cylindrical envelope and which has side walls facing outwardly of the cylindrical envelope with holes therein for delivery of liquid to a site of placement in a vessel where the stent is placed. The stent may be positioned in one of two states, one state being where the stent assumes the shape of an enlarged generally cylindrical envelope and the other state being where the stent assumes the shape of a contracted smaller cylindrical envelope. In a specific embodiment, holes are small enough to prevent rapid leakage, but large enough to allow slow leakage of a liquid solution from the stent over a period of several hours to a week or more. In a specific embodiment, the stent is made of a nickel titanium alloy. The hollow tubular wire stent may extend in an undulating helical path to form the cylindrical envelope.

U.S. Pat. No. 5,733,327 describes a stent body produced by weaving or knitting a fiber containing a drug and made of a low-melting biodegradable polymer into a tubular shape, or coating a drug-containing low-melting biodegradable polymer on a stent body. When the stent is introduced into the vascular system, the drug contained therein is dosed in a locally limited region of the vascular system. The low-melting biodegradable polymer used has a melting point of 80° C. or lower and may comprise poly-ϵ-caprolactone, poly-D, L-deca-lactone, poly-dioxane or a copolymer thereof.

In U.S. Pat. No. 5,843,172, there is a metallic stent configured to maintain patency of a human vessel, the metallic stent having a plurality of porous cavities; a therapeutic medication loaded into the porous cavities of the metallic stent; and a polymeric coating over the surface of the metallic stent, wherein the medication in the pores of the stent is a first medication, wherein the coating contains a second medication.

An expandable intraluminal stent comprising a main body portion is described in U.S. Pat. No. 5,972,027, having a first end, a second end and a flow passage defined therethrough. The main body portion is sized for intraluminal placement within a body passage and subsequent expansion for implantation, and at least a portion of the main body portion is formed of at least one material having pores therein. The material is formed from at least one powdered metal, and the stent comprises at least two separate regions arranged along the length of the stent, the first region formed of a first material having first pores within, and the second region formed of a second material having second pores within. In specific embodiments, at least one of the first and second regions has a porosity of twenty to eighty percent by volume. In another specific embodiment, at least one of the first and second regions has a porosity of between forty and sixty percent of the total volume of the metal. The stent may be further defined as formed of a plurality of strands of a metal, the metal having pores therein. Also, the stent may be coated with one or more layers of one or more drug-containing materials. Furthermore, the first or second powdered metal may be stainless steel, and the pores in the first and second materials may contain at least one drug.

In specific embodiments, the stent is coated with an amount of nitric oxide effective to inhibit platelet aggregation that would otherwise be promoted by contact of the blood with the stent, as described in U.S. Pat. No. 5,797,887.

B. Avicins

The triterpene compounds (avicins) of the invention were originally identified from a targeted screening of 60 plant extracts from selected leguminous species native to arid and semi-arid regions. Of the initial screening, one extract, designated UA-BRF-004-DELEP-F001 and isolated from *Acacia victoriae* (Benth.) (Leguminosae), showed potent anti-tumor activity against a variety of human tumor cell lines. This extract was subsequently further purified into various fractions. In two rounds of purification, an extract was identified which comprised the purified anti-tumor compounds. This extract was identified to contain purified triterpene glycoside saponins. A procedure was subsequently developed for the efficient isolation of the active compounds. These compounds and purification procedures are further addressed in U.S. Patent Application Ser. No. 60/099,066, filed Sep. 3, 1998, and U.S. Patent Application Ser. No. 60/085,997, filed May 19, 1998.

In specific embodiments of the invention, the avicin compound comprises activities other than anti-tumor activity. In part, the stent utilizes Avicin D, Avicin G, or a combination thereof, for example. Avicin D is a colorless amorphous solid. The molecular weight is 2,104 atomic mass units (amu), according to matrix-assisted laser desoprtion ionization (MALDI). The molecular formula is $C_{98}H_{155}NO_{46}$. In further specific embodiments, Avicin D is a saponin with a side chain comprising two units of acyclic monoterpene, trans-2-hydroxymethyl-6-methyl-6-hydroxy-2,7-octadienoic acid connected by a quinovose sugar and attached to acacid acid at carbon 21; a trisacchardie at carbon 3 and a tetrasaccharide at carbon 28 are also present. Avicin G, which is also comprised in fraction F094, has a molecular weight of 2,065. The side chain is similar to avicin D, although the outer monoterpene is replaced by trans-2,6-dimethyl-6-hydroxy-2,7-octadienoic acid.

The avicin compounds utilized in the present invention may be prepared by obtaining tissue from an *Acacia victoriae* plant; extracting the tissue with a solvent; and obtaining one or more triterpene glycosides. The tissue may comprise a pod, a root, a seedling, or a combination thereof. In specific embodiments, the solvent is methanol, ethanol, isopropyl alcohol, dichloromethane, chloroform, ethyl acetate, water, glycerol or a mixture thereof. The process may further comprise isolating the composition from plant bagasse by filtration after the extracting. The process may also further comprise defatting with an organic solvent prior to extracting. In a specific embodiment, the organic solvent is hexane, dichloromethane, chloroform, ethyl acetate or a mixture thereof. In another specific embodiment, the obtaining comprises isolating at least one triterpene glycoside chromatographically, such as by isolating by elution with methanol, acetonitrile, water, or a mixture thereof. The composition may be isolated using liquid chromatography. In specific embodiments, the method further comprises evaporating the solvent after the extraction.

In another method of preparing an avicin for the invention, there is preparing a tissue culture comprising cells of an *Acacia victoriae* plant; and extracting the triterpene glycoside composition from the culture with a solvent, such as methanol, ethanol, isopropyl alcohol, dichloromethane, chloroform, ethyl acetate, water or a mixture thereof. The tissue culture may comprise a hairy root culture, for example. The tissue culture may be prepared by any suitable means in the art, including infecting *Acacia victoriae* cells with *Agrobacterium rhizogenes* R-1000. In specific embodiments, the tissue culture comprises from about 3% to about 4% sucrose by weight. The method may further comprise filtering plant bagasse from the triterpene glycoside composition after extraction. The method may also further comprise isolating the triterpene glycoside composition by liquid chromatography after the extraction. The method may also further comprise evaporating the solvent after the extraction.

It is contemplated that certain benefits for the stents may be achieved by utilizing avicins suited with novel characteristics, such as a longer in vivo half-life or other beneficial properties, such as improved anti-inflammatory and/or anti-proliferative properties. Such avicins may be produced by manipulating or modifying mixtures of avicins or an individual avicin molecule itself, for example through modification or removal of sugars and/or conjugation of avicins to inert carriers, such as various protein or non-protein components, including immunoglobulins and Fc portions. It will be understood that longer half-life is not coextensive with the pharmaceutical compositions for use in "slow release." Slow release formulations are generally designed to give a constant drug level over an extended period. Increasing the half-life of an avicin for use on a stent of the present invention is intended to result in higher or longer-lasting local delivery levels upon administration of the stent to the vessel.

II. THE PHARMACEUTICAL NATURE OF THE TRITERPENE COMPOSITIONS FOR THE INVENTION

The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art, and in the present invention may be employed to enhance functionality and/or delivery of the avicin. Except insofar as any conventional media or agent is incompatible with the active ingredient, its use in the therapeutic compositions is contemplated. Supplementary active ingredients also can be incorporated into the compositions.

The avicin compositions have anti-proliferative activities and work by several mechanisms to induce apoptosis in cancer cells; in other embodiments they have anti-inflammatory properties, for example. Pharmaceutical compositions of these compounds are envisioned as powerful drugs for restenosis that may be used by themselves in a stent or in combination with other forms of therapy. One of skill in the art will determine the effective dosages and the combination therapy regimen.

III. PREPARATION OF THE DRUG-COATED STENT OF THE INVENTION

Generation of the avicin-encompassed stent can be loaded directly onto the surface of the stent by simple dip-coating and/or spray-coating techniques. In other embodiments, a polymeric matrix is utilized, such as for controlled release of the avicin(s), wherein the avicins are either covalently or non-covalently bound. Avicin compounds for application to stents are described in U.S. Pat. No. 6,444,233, the entire disclosure of which is specifically incorporated herein by reference.

An inert coating matrix may be preferred. The matrix comprising the drug and the polymer may also be dipped or spray-coated. In embodiments wherein non-biodegradable matrixes are utilized (such as, for example, methacrylate), the avicin can be released by particle dissolution or diffusion. When biodegradable matrices (such as, for example, poly-L-lactic acid (PLLA)) are utilized, the avicin can be released upon polymer breakdown. Another example of a coating is phosphorylcholine, which can act as a reservoir for programmed elution of avicin via the wet dip coating method, wherein a nonexpanded stent is placed into an avicin solution, followed by air drying to allow evaporation of the solvent, such as ethanol, and attachment of the avicin to the stent. In other embodiments, the stents comprise two or more coatings of avicin.

IV. USE OF THE STENTS OF THE INVENTION

Placement of the stent into the vessel encompasses a variety of parameters, and there may be correct sizing of the stent length to match the length of the lesion, or blocked area; correct sizing of the stent diameter to match the thickness of the healthy part of the artery; and/or sufficient deployment of the stent, making sure that the stent, once placed at the optimum site in the blocked artery, is expanded fully to the arterial wall. In cases wherein there is under-expansion of the stent, small gaps between the stent and arterial wall can result, leading to serious problems such as blood clots, or Sub-Acute Thrombosis (SAT). These difficulties can be overcome by the sizing and the assessments of expansion, such as by viewing the real-time angiogram in the cath lab, although in other embodiments intravascular ultrasound imaging may be employed.

In specific embodiments, a coronary stent is collapsed to a small diameter and placed over a balloon catheter. Upon moving it into the area of the blockage, the balloon is inflated, the stent expands, and then locks in place to form a scaffold that holds the artery open. The stent may be permanent or it may be temporary. In particular embodiments, stents reduce the renarrowing that occurs after balloon angioplasty or other procedures that use catheters. Stents also help restore normal blood flow and keep an artery open if it has been torn or injured by the balloon catheter.

In general embodiments of the invention, a stent is inserted through a main artery in the groin (femoral artery) or arm (brachial artery) and threaded up to the narrowed section of the artery with a tiny catheter (balloon catheter.)

When it reaches the right location, the balloon is slightly inflated to push the plaque out of the way and expand the artery (balloon angioplasty). Some stents are stretched open (expanded) by the balloon at the same time as the artery. Other stents are inserted into the artery immediately after the angioplasty procedure.

An intraluminal coronary artery stent is a small, self-expanding, stainless steel mesh tube that is placed within a coronary artery to keep the vessel open. It may be used during a coronary artery bypass graft surgery to keep the grafted vessel open, after balloon angioplasty to prevent reclosure of the blood vessel, or during other heart surgeries.

V. RESTENOSIS

Restenosis refers to the reoccurrence of stenosis (a narrowing or constriction of the diameter of a bodily passage or orifice) in a blood vessel or heart valve after it has been treated (such as by balloon angioplasty or valvuloplasty, for example), and it usually occurs within about 6 months after the initial procedure. In specific embodiments, the treated vessel becomes blocked again, at least partially. Given the reduced chance of restenosis occurring with the use of stents, the majority of current patients having angioplasty are treated with stents. Those in the art consider "restenosis" not to be the progression of coronary artery disease, but rather the body's immune system response to the "injury" of the angioplasty. In particular, it is characterized by growth of smooth muscle cells—roughly analogous to a scar forming over an injury.

There are two major mechanisms for restenosis. The first is by thrombosis, or blood clotting, at the site of treatment, particularly when the risk of thrombosis is the greatest immediately after angioplasty, because the resultant tissue trauma tends to trigger blood clotting. This form of restenosis is greatly reduced by using anti-clotting drugs for a time during and after the procedure. The second form of restenosis is tissue growth at the site of treatment. This form of restenosis—a proliferation of the endothelial cells that normally line blood vessels—tends to occur during the first 3 to 6 months after the procedure, and is not prevented by anti-clotting drugs. It can be thought of as resulting from excessive tissue healing and regeneration, on the order of scar formation, after the trauma of angioplasty. The avicins of the present invention may be useful for one or both forms of restenosis.

In a particular embodiment of the present invention, the tissue growth form of restenosis may be treated. In specific embodiments, restenosis occurs after the use of stents, which is referred to as "in-stent restenosis," wherein new tissue grows inside the stent, such as through covering the struts of the stent. Although this new tissue comprises healthy cells from the lining of the arterial wall (endothelium) and is considered desirable because development of normal lining over the stent allows blood to flow smoothly over the stented area without clotting, in some embodiments scar tissue may form underneath the new healthy lining. In about 25% of patients, the growth of scar tissue underneath the lining of the artery is thick enough that it can obstruct the flow of blood and produce an important blockage. Most in-stent restenosis occurs about 3 to 6 months after the procedure, although it is unusual to find in-stent restenosis occur after about 12 months.

In particular embodiments, in-stent restenosis results from intimal hyperplasia, wherein platelets are activated, form thrombi, and release their granular contents. With the assistance of cytokines and growth factors released from wounded cells in the vessel wall, inflammatory cells are recruited and smooth muscle cell migration and proliferation is stimulated. The SMCs form an extracellular matrix, thereby ultimately resulting in an exaggerated intimal process, which is maintained by chronic inflammatory mechanisms. That is, the process is further defined as invoking adherence of circulating inflammatory cells, such as neutrophils, monocytes, and lymphocytes, to the wound site, and migration into a thrombus. Finally, vascular remodeling comprising adventitial fibroblast proliferation, transformation to myofibroblasts, adventitial thickening (or constriction), and increasing cell density may occur in the process of vascular remodeling. Thus, in specific embodiments of the invention, avicins are well-suited to treatment of in-stent restenosis, wherein the avicins comprise anti-thrombotic, anti-inflammatory, and/or anti-mitotic agents.

Symptoms of in-stent restenosis are very similar to classic cardiovascular disease symptoms, such as chest pain triggered by exertion. Diabetic patients, who are considered high risk for in-stent restenosis, however, may have fewer symptoms, atypical and unusual symptoms, or even no symptoms at all.

The patient with restenosis may be taking an anti-clotting drug, such as aspirin, clopidogril or ticlopidine (brand names Plavix and Ticlid), for example, for a period of time after the stenting (such as up to six months) to prevent the blood from reacting to the new device by thickening and clogging up the newly expanded artery (thrombosis). Preferably, a smooth, thin layer of endothelial cells (the inner lining of the blood vessel) grows over the stent during this period and the device is incorporated into the artery, reducing the tendency for clotting.

VI. THERAPEUTIC KITS

The present invention also provides therapeutic kits comprising the avicin compositions described herein; a suitable stent; or both. Such kits will generally comprise, in suitable container means, a pharmaceutically acceptable formulation of at least one avicin compound in accordance with the invention. The kits also may contain other pharmaceutically acceptable formulations, such as those components to facilitate delivery of the avicin compound to the endothelial cells of the vessel, to enhance or provide the treatment of restenosis, to enhance or provide the treatment of coronary artery disease, or any one or more of a range of drugs that may work in concert with the avicin compounds, for example, anti-proliferative agents such as rapamycin or Taxol.

The kits may have a single container means that contains the avicin compounds, with or without any additional components, or they may have distinct container means for each desired agent. When the components of the kit are provided in one or more liquid solutions, the liquid solution is an aqueous solution, with a sterile aqueous solution being particularly preferred. However, the components of the kit may be provided as dried powder(s). When reagents or components are provided as a dry powder, the powder can be reconstituted by the addition of a suitable solvent. It is envisioned that the solvent also may be provided in another container means. The container means of the kit will generally include at least one vial, test tube, flask, bottle, syringe or other container means, into which the avicin, and any other desired agent, may be placed and, preferably, suitably aliquoted. Where additional components are included, the kit will also generally contain a second vial or other container into which these are placed, enabling the administration of separated designed doses. The kits also may comprise a second/third container means for containing a sterile, pharmaceutically acceptable buffer or other diluent.

The kits also may contain a means by which to administer the avicin compositions to the stent. The kits of the present invention will also typically include a means for containing the vials, or such like, and other component, in close confinement for commercial sale, such as, e.g., injection or blow-molded plastic containers into which the desired vials and other apparatus are placed and retained. In certain aspects the kits include information concerning instructions for preparation and/or delivery of the stent.

VI. COMBINATION TREATMENT

In certain embodiments of the present invention, it may be desirable to administer the compositions of the invention in combination with one or more other agents. For example, the one or more agents may be blood-thinning (anti-platelet or anti-clotting) medication, such as aspirin, heparin, and so forth. In other embodiments, additional coronary disease treatments may be employed, such as drugs, surgery, procedures, or lifestyle changes. This may enhance the overall activity achieved by therapy with the compounds of the invention alone, or may be used to prevent or combat additional coronary artery disease problems.

To use the present invention in combination with the administration of a second coronary artery disease therapy, restenosis therapy, or both, one would simply administer to an animal a stent/triterpene composition in combination with the second therapy in a manner effective to result in their combined actions within the animal. The stent/triterpene composition and second therapy may be administered to the animal simultaneously or in succession. The intervals for the inventive therapy and second therapy may range from minutes to weeks, for example. In embodiments where the second agent and stent/triterpene composition are administered separately to the animal, one would generally ensure that a significant period of time did not expire between the time of each delivery, such that the additional therapy and stent/triterpene composition would still be able to exert an advantageously combined effect on the vessel. In such instances, it is contemplated that one would contact the vessel with both agents within about 5 minutes to about one week of each other and, more preferably, within about 12-72 hours of each other, with a delay time of only about 24-48 hours being most preferred. In some situations, it may be desirable to extend the time period for treatment significantly, where several days (2, 3, 4, 5, 6 or 7) or even several weeks (1, 2, 3, 4, 5, 6, 7, 8, or more) lapse between the respective administrations. It also is conceivable that more than one administration of either the stent/triterpene composition or the second agent will be desired.

Another particularly significant use contemplated for the compounds of the invention is as an anti-inflammatory agent. The inventor have shown that the active triterpene compounds of the invention are potent inhibitors of transcription factor NF-κB, which plays an important role in the inflammatory response. This finding is particularly significant given the increasing amount of evidence suggesting the central role of inflammatory response in carcinogenesis. Treatment of patients with the triterpene compounds provided herein may, therefore, potentially alleviate a wide degree of ailments associated with inflammation, including tissue damage.

The initial stages of an inflammatory response are characterized by increased blood vessel permeability and release (exudation) of histamine, serotonin and basic polypeptides and proteins. This is accompanied by hyperaemia and oedema formation. Subsequently, there is cellular infiltration and formation of new conjunctive tissue. It is believed that treatment with the compounds of the invention can limit these early stages of inflammation and, thereby, decrease the negative effects associated with the inflammatory condition.

VII. DEFINITIONS

"A" means "one or more." Thus, a moiety may refer to one, two, three, or more moieties.

Avicin as used herein refers to a triterpene saponin, such as one from the *Acacia victoriae* plant. In particular, avicin compounds are obtained from the roots and pods of the *Acacia victoriae* plant.

Restenosis as used herein refers to the reoccurrence of stenosis (a narrowing or constriction of the diameter of a bodily passage or orifice) in a blood vessel or heart valve after it has been treated (as by balloon angioplasty or valvuloplasty).

Saponin as used herein refers to a plant glucoside with a steroid structure that forms soapy lather when mixed and agitated with water.

Stent as used herein refers to any material that is used to hold tissue in place, such as, for example, a device inserted into a tubular structure, such as a blood vessel, that acts as a structural scaffold for the tubular structure.

Terpene as used herein refers to a compound having the molecular formula $(C_5H_8)n$, having at least one isoprene unit and classified according to the number of isoprene ($CH_2$=C($CH_3$)—CH=$CH_2$) units.

Therapeutically Effective as used herein refers to an amount of an avicin supplied at least on the stent that results in improvement of at least one symptom of a condition being treated by the stent, such as restenosis, or that prevents at least one symptom of the condition. The at least one symptom that is improved may be detectable at the molecular level, such as reducing, inhibiting, and/or preventing a molecular pathway that results in the mechanisms associated with the condition, such as restenosis, such as inhibiting the activation of NF-κB, for example. The at least one symptom that is improved may be detectable at the cellular level, such as inhibiting formation of neotimal hyperplasia and/or inhibiting vascular smooth muscle cell proliferation and/or migration. Also, the at least one symptom that is improved may be at the organismal level, such as decrease in chest pain, for example.

Triterpene or Triterpene Glycoside refers to the novel and/or biologically active saponin compounds identified herein from *Acacia victoriae*. The triterpene or triterpene glycosides need not be isolated from *Acacia victoriae*, as one of skill in the art, in light of the instant disclosure, could isolate the compounds from related species, or chemically synthesize analogs of the triterpenes and triterpene glycosides disclosed herein. "Triterpenes" of this invention include the saponin compounds described herein which have at least a triterpene unit(s) and, in the case of triterpene glycosides, a sugar or saccharide. These terms also refer to compounds containing additional moieties or chemical functionalities including, but not limited to, monoterpene units as will be apparent from the rest of the specification. Thus, triterpenes of this invention also include the aglycones formed by hydrolysis of sugar units and further includes other modification of the triterpenoid compounds, whereby the modifications do not destroy the biological activity of the compounds.

XII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Exemplary Avicins

Avicin D1, Avicin G1, and Avicin B1

1.1 The Structure of D1

D1 is a major component of *Acacia victoriae* pods. Assays of this compound show that it has considerable biological activity.

1.1.1. Whole Molecule D1

D1 was isolated as a colorless amorphous solid isolated from the partially purified extract F094 obtained using several preparative HPLC separations as described in the examples above. Its molecular weight from MALDI mass spectroscopy is 2104 amu which is the sodium adduct of 2081, the true molecular weight. A high resolution FAB mass spectroscopy confirmed this molecular weight and gave the molecular formula of $C_{98}H_{155}NO_{46}$. Such a molecule is too large for structure determination via spectroscopy alone and so a degradation program was undertaken as outlined in Scheme 1 shown in FIG. 1. In FIG. 1, D1 is represented by the structure labeled '(1)'.

The proton and carbon NMRs of D1 showed the presence of a triterpene, two monoterpenes and approximately eight sugars (See Table 2 for selected $^{13}$C-NMR assignments under (1)).

TABLE 2

$^{13}$C NMR (MeOH-d4) assignments of D1(1), G1(14), B1(21), Aglycone (2) and Acacic acid (3). (The numbers in brackets i.e., 1, 14, 21, 2 and 3, refer to structures of D1, G1, B1, Aglycone and Acacic acid, depicted in FIG. 1, FIG. 2 and FIG. 3 respectively.)

| Carbon No. | (1) | (14) | (21) | (2) in DMSO-d6 | (3) |
|---|---|---|---|---|---|
| Triterpene Part | | | | | |
| 1 | 36.13 | 36.13 | 36.13 | 36.07 | 38.90 |
| 2 | 27.15 | 27.15 | 27.15 | 29.28 | 28.03 |
| 3 | 89.86 | 89.84 | | 76.78 | 77.94 |
| 4 | | 40.09 | 39.85 | 39.71 | 39.28 |
| 5 | | 57.08 | | 54.84 | 55.78 |
| 6 | | 19.54 | | 18.03 | 18.71 |
| 7 | 34.59 | 34.59 | 34.58 | 34.27 | 33.51 |
| 8 | | 40.82 | 40.09 | 40.82 | 39.79 |
| 9 | | 48.08 | | 46.11 | 47.15 |
| 10 | | 37.94 | 37.94 | 36.59 | 37.31 |
| 11 | 24.29 | 24.54 | 24.49 | 26.97 | 23.77 |
| 12 | 124.04 | 124.04 | 124.09 | 122.04 | 122.61 |
| 13 | 143.70 | 143.7 | 143.68 | 142.61 | 144.29 |
| 14 | | 42.64 | 42.63 | | 42.01 |
| 15 | 36.20 | 36.39 | 36.51 | | 35.74 |
| 16 | | 74.26 | | 72.41 | 74.22 |
| 17 | | 52.29 | | 49.70 | 51.67 |
| 18 | | 41.64 | 41.60 | | 40.97 |
| 19 | 48.67 | 48.3 | | 46.85 | 48.42 |
| 20 | | 35.88 | 35.95 | | 36.64 |
| 21 | | 78.61 | | 76.78 | 73.32 |
| 22 | 39.86 | 41.7 | 41.94 | 38.07 | 41.97 |
| 23 | 28.62 | 28.61 | 28.65 | 26.60 | 28.65 |
| 24 | 17.12 | 17.11 | 17.11 | 16.06 | 15.55 |
| 25 | 16.22 | 16.22 | 16.25 | 15.19 | 16.47 |
| 26 | 17.73 | 17.72 | 18.07 | 16.78 | 17.43 |
| 27 | 27.40 | 27.32 | 27.40 | 28.24 | 27.11 |
| 28 | 173.39 | 175.34 | 175.39 | 176.64 | 179.14 |
| 29 | 29.41 | 29.43 | 29.41 | 28.77 | 29.97 |
| 30 | 19.42 | 19.42 | 19.53 | 18.65 | 18.26 |
| Outer Monoterpene | | | | | |
| 1 | 168.69 | 168.68 | 168.74 | | |
| 2 | 132.92 | 132.92 | 132.82 | | |
| 3 | 148.48 | 148.02 | | | |
| 4 | 24.49 | 24.58 | 24.56 | | |
| 5 | 41.95 | 41.33 | 40.83 | | |
| 6 | 81.01 | 81.0 | | | |
| 7 | 145.93 | 144.01 | | | |
| 8 | 112.53 | 112.44 | 112.53 | | |
| 9 | 16.75 | 16.7 | 16.74 | | |
| 10 | 56.51 | 12.49 | | | |
| Inner Monoterpene | | | | | |
| 1 | 168.17 | 169.01 | 168.19 | 164.0 | |
| 2 | 132.49 | 128.52 | 132.49 | 135.20 | |
| 3 | 148.03 | 145.95 | | 137.05 | |
| 4 | 24.29 | 24.29 | 24.30 | 22.86 | |
| 5 | 41.33 | 39.86 | 39.73 | 76.03 | |
| 6 | | 73.61 | | 129.41 | |
| 7 | 144.03 | 144.43 | | 119.80 | |
| 8 | 116.0 | 116.0 | 115.33 | 11.86 | |
| 9 | 23.76 | 23.7 | 24.21 | 12.81 | |
| 10 | 56.62 | 56.61 | | 64.28 | |

1.1.2. Vigorous Acid Hydrolysis of D1

Hydrolysis of D1 in 3N HCl at 100° C. for 2 hrs. produced "D1 aglycone", depicted as (2) in FIG. 1, which was shown by mass spectroscopy to have a molecular weight of 652. The NMR of D1 aglycone showed the presence of a triterpene and a modified monoterpene but no sugars. This material was further degraded by saponification (1.3N NaOH at 100° C. for 30 min. in MeOH) from which the following were isolated:

1.1.2.a. Triterpene The C-13 NMR of this material was identical with that reported previously for acacic acid (see FIG. 1 structure depicted by (3), and see Table 12 for $^{13}$C-NMR assignments under (3)) and its molecular weight by mass spectroscopy at 488 is consistent with this structure.

1.1.2.b. Cyclized Monoterpene The molecular weight and NMR of this compound indicated the presence of a carboxylic acid, two methyl groups attached to a double bond and two vinyl protons leading to the pyrane structure indicated. While this structural unit Structure depicted by (4) FIG. 1, was also present in "D1 aglycone", it was not present in the parent D1. The D1 contains the acyclic monoterpene, depicted as structure (5) in FIG. 1, and this structure undergoes cyclization during the acid hydrolysis as shown below:

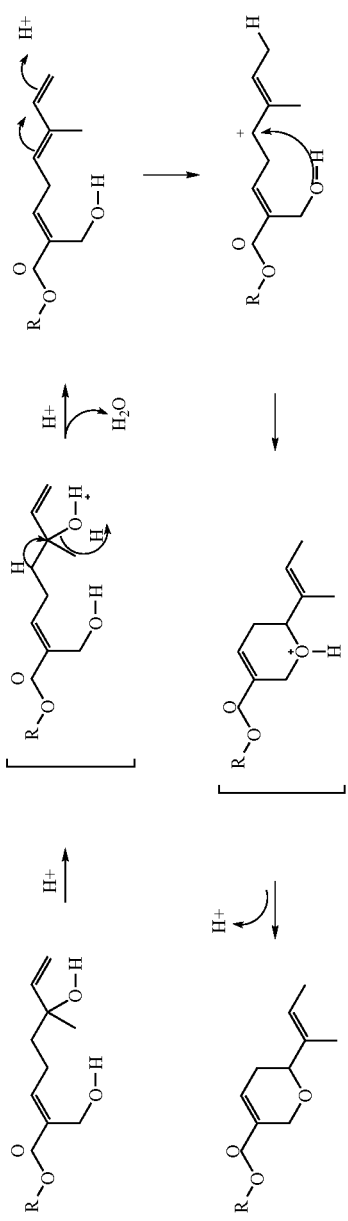

These structures along with the original molecular weight and spectral characteristics of D1 fit well with the structure of D1 aglycone depicted in FIG. 1 by the structure labeled (2). See Table 11 for selected $^{13}$C-NMR assignments under (2).

1.1.3. Mild Saponification of D1

When D1 was treated with 0.5N NH$_4$OH at room temperature for 1 hour there was complete conversion into two new compounds.

1.1.3.a. Monoterpene This molecule had a molecular weight of 200 and NMR which indicated that it possessed an acyclic monoterpene structure, supporting the suspected degradation. This structure is depicted in FIG. 1 and is labeled (5).

1.1.3.b. Triterpene Monoterpene Oligosaccharide This compound is more polar than D1 and its NMR is consistent with it containing acacic acid, one monoterpene and several monosaccharides. This structure is depicted in FIG. 1 and is labeled (6).

1.1.4. Sugar Analysis of D1

A vigorous acid hydrolysis of D1 (2N HCl at 100° C. for 2 hours) followed by derivatization (trimethylsilyl ethers) and GC/MS analysis confirmed the presence of eight sugar residues in the original molecule: arabinose, rhamnose, fucose, xylose, 6-deoxyglucose (i.e. quinovose), N-acetyl glucosamine and two molecules of glucose.

1.1.5. More Aggressive Saponification of the Triterpene Monoterpene Oligosaccharide When the triterpene monoterpene oligosaccharide was subjected to 0.3N NaOH for 1 hour at 60° C. three compounds were formed:

1.1.5.a. Oligosaccharide Isolation and analysis of this very polar fragment suggested that it was an oligosaccharide. Sugar analysis performed by acid hydrolysis (2N HCl at 100° C. for 2 hours) and GC/MS analysis of the trimethylsilyl ethers of the monosaccharides confirmed that the oligosaccharide was a tetrasaccharide made up of two molecules of glucose and one each of arabinose and rhamnose.

1.1.5.b. Monoterpene Glycoside This material has NMR's consistent with structure (8) depicted in FIG. 1. Acid hydrolysis (2N HCl at 100° C. for 2 hours) of this compound led to the identification of the sugar as 6-deoxy glucose. Treatment of this monoterpene glycoside with β-glucosidase gave the monoterpene with the structure depicted by (9) in FIG. 1, which has an NMR consistent with trans-2-hydroxymethyl-6-hydroxy-6-methyl-2,7-octadienoic acid. Hydrolysis of this linkage with a "beta"-glucosidase indicates that the linkage between these two groups is a beta linkage.

1.1.5.c. Triterpene Glycoside This compound has a molecular weight of 951 and NMR's which is consistent with the acacic acid lactone containing a trisaccharide at the C-3 position depicted by structure (10b) in FIG. 1. Acid hydrolysis (2N HCl at 100° C. for 2 hours) of this compound allowed the identification of its constituent sugars as N-acetyl glucosamine, fucose, and xylose by GC/MS as trimethyl silyl derivatives. This molecule was observed in both the open acid/alcohol, which is depicted in FIG. 1 by the structure labeled (10a), and the closed lactone form, which is depicted in FIG. 1 by the structure labeled (10b).

Sugar analysis and molecular weight of the fragments as compared with those in the whole molecule D1 confirmed that all portions of D1 were accounted for in fragments depicted by structures labeled (5), (7), (8), and (10a) in FIG. 1.

1.1.6. Mild Acid hydrolysis of D1

Mild acid hydrolysis of D1 (1N HCl for 16 hrs at 25° C.) allowed the formation of two new molecules:

1.1.6.a. Monoterpene Sugar The molecular weight, NMR spectra, and sugar analysis were consistent with a monoterpene-6-deoxyglucose. The structure of this molecule is depicted in FIG. 1 by the structure labeled (11).

1.1.6.b. Triterpene-Monoterpene-Glycoside The second molecule was identified to be a triterpene-monoterpene-glycoside and the structure of this molecule is depicted in FIG. 1 by the structure labeled (12).

1.1.7. The attachment of subgroups within D1

NMR studies indicate that the carboxylic acid of the outer monoterpene is esterified to C-4 of 6-deoxyglucose (quinovose). NMR and hydrolysis studies have shown that the anomeric carbon of the quinovose is attached to the C-6 hydroxy group of the inner monoterpene. The stereochemistry at the anomeric carbon of quinovose indicate a "beta" linkage.

Figure 4:
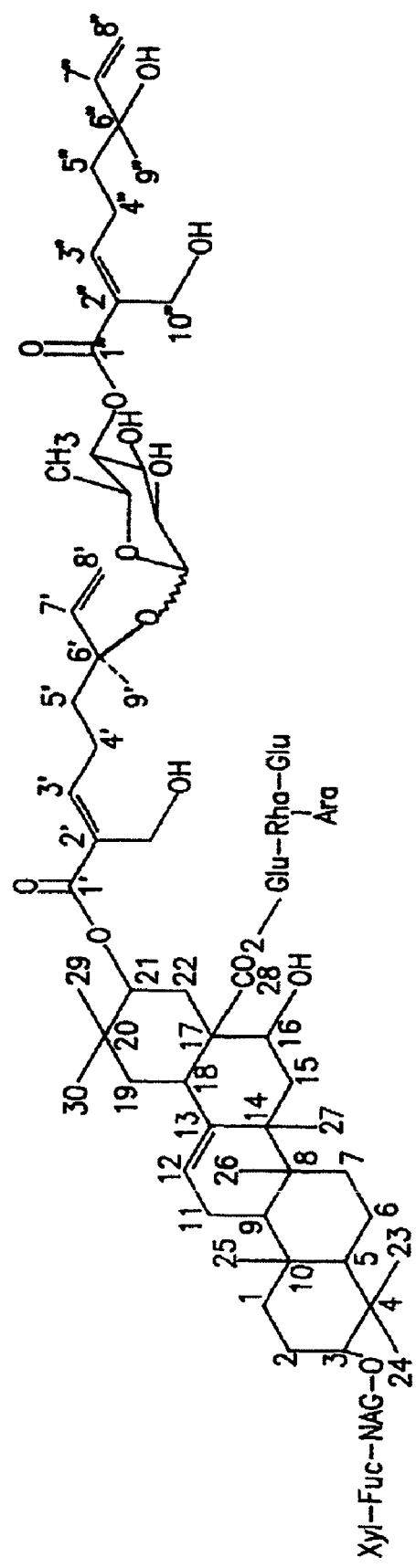
FIG. 4: Structure of triterpene glycoside D1.

Hydrolysis (2N HCl for 2 hrs at 100° C.) and sugar isomerization studies indicate that the sugars in the tetrasaccharide are two molecules of glucose, and one molecule each of rhamnose and arabinose. The unit is directly esterified to the C-28 carboxylic acid of the triterpene as shown in FIG. 4. Iron trap mass spectroscopy studies indicate that the tetrasaccharide structure has two glucose and one arabinose attached to a central rhamnose as shown in FIG. 4. The linkage of these sugars one to another is still unknown.

NMR studies indicate that N-acetyl glucosamine (NAG) is attached directly to the C-3 carbon of the triterpene. The remainder of the sequence of the sugars is fucose in the middle and xylose on the end by LC/MS studies of partial hydrolysis (1N HCl for 1 hr at 60° C. in 50% MeOH). The linkage of these sugars one to another is still unknown.

1.1.8. Elliptoside E

D1 contains a triterpene and two monoterpenes commonly found in saponins reported from other species including other *Acacia*. Although the structure of D1 is similar to elliptoside E, (FIG. 5), reported from *Archidendron ellipticum*, (Beutler et al., 1997). In the present invention, the specific rotation of D1 has been determined to be $[\alpha]_D = -30.0°$ which is different than the reported value for elliptoside E at −24.3°.

Elliptoside E, described in Beutler et al. (1997, and D1 have different HPLC retention times (D1—15.2 min., elliptoside E—12.5 min.). Therefore, these two molecules must differ in some manner such as the specific attachment of their subunits or from the presence of optical or structural isomers.

The inventor observed that the specific rotation of the inner monoterpene, depicted by structure (9) in FIG. 1, is +11.2° in MeOH and +16° in chloroform. This same fragment in elliptoside E was reported to be −9.1° in chloroform. Furthermore, the only chiral center of the inner monoterpene of D1 was determined to have an "S" configuration which is opposite to that found in elliptoside E. The specific rotation of the outer monoterpene of D1 is being sought at this time. Furthermore, proton NMR shows that the monoterpene double bonds in D1 are "trans" whereas the monoterpene double bonds are "cis" in elliptoside E as shown in Beutler et al., 1997. These two features constitutes the first structural differences found between D1 and elliptoside E. Enzymatic catalytic hydrolysis of specific sugars has shown that the arrangements of sugars is the same as in elliptoside E.

1.2. The Structure of G1

Biological assays of this material shows that G1 is more biologically active than D1.

1.2.1. Whole Molecule G1 (14)

The second structure determined in the present invention was G1. It was also isolated from F094 by prep HPLC but in low compound recovery. G1 is slightly less polar than D1. The molecular weight by MALDI mass spectroscopy indicates a molecular weight of 2065 which is 16 amu less than D1. Specific rotation of G1 was found to be −26.9° (MeOH). The proton NMR shows that G1 is also a saponin, very similar to D1 and indicates that it only differs from D1 by having one less oxygen in the outer monoterpene which is now trans-2, 6-dimethyl-6-hydroxy-2,7-octadienoic acid. See FIG. 2, structure labeled (14), and Table 11 for selected $^{13}$C-NMR assignments under (14). G1 was degraded as shown in Scheme 2, FIG. 2.

1.2.2. Mild Saponification of G1

When G1 was treated with 0.5 N NH$_4$OH at room temperature for even a few minutes there is complete conversion into the more polar mild saponification product and a monoterpene.

Figure 2:
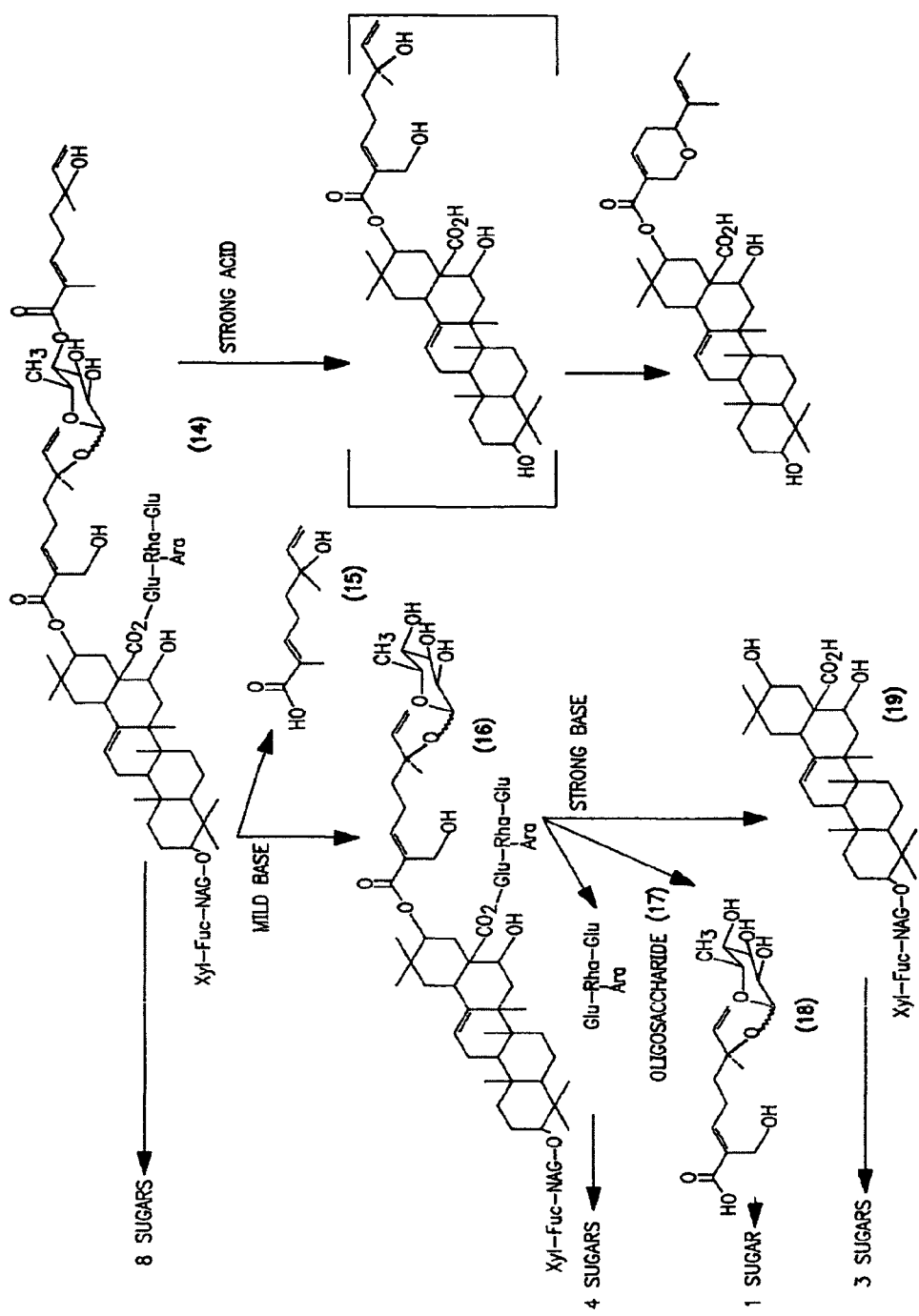
FIG. 2: Depicts compounds from the degradation of compound G1.

1.2.2.a. Monoterpene The molecular weight and NMR of this material indicates that it possesses a methyl group at the C-2 position where a hydroxymethyl had been in. This is depicted in FIG. 2 by the structure labeled (15).

1.2.2.b. Triterpene Monoterpene Oligosaccharide The NMR of this compound indicates that it was identical by HPLC retention time and by proton NMR with the structure labeled (16) depicted in FIG. 2, which is similar to the structure labeled (6) in FIG. 1 made from D1 and that it contains an acacic acid, one monoterpene and eight monosaccharides as was seen in D1. The similarity of (16) with (6) indicates a similar stereochemistry seen in D1 inner monoterpene.

1.2.3. Sugar Analysis of G1

A vigorous acid hydrolysis of G1 (2N HCl at 100° C. for 2 hours) produced the same monosaccharide units as were present in D1: arabinose, rhamnose, fucose, xylose, 6-deoxyglucose, N-acetyl glucosamine and two molecules of glucose.

1.2.4. Acid Hydrolysis of G1

An acid hydrolysis of the mild saponification product allowed the isolation of three molecules in a manner as in D1. NMR and sugar analyses (2N HCl at 100° C. for 2 hours) were performed on each. This is depicted in FIG. 2 by the structure labeled (16).

1.2.4.a. Oligosaccharide contained two molecules of glucose and one each of arabinose and rhamnose and is depicted in FIG. 2 by the structure labeled (17).

1.2.4.b. Monoterpene Glycoside contained an acyclic monoterpene (depicted in FIG. 2 by the structure labeled (5)), and 6-deoxyglucose and the whole structure is depicted in FIG. 2 by the structure labeled (18).

1.2.4.c. Triterpene Glycoside contained acacic acid and one molecule each of N-acetyl glucosamine, fucose, and xylose. The sugars in these fragments are arranged in the same order as in D1. This structure is depicted in FIG. 2 by the structure labeled (19).

1.2.5. Elliptoside A

Figure 5:
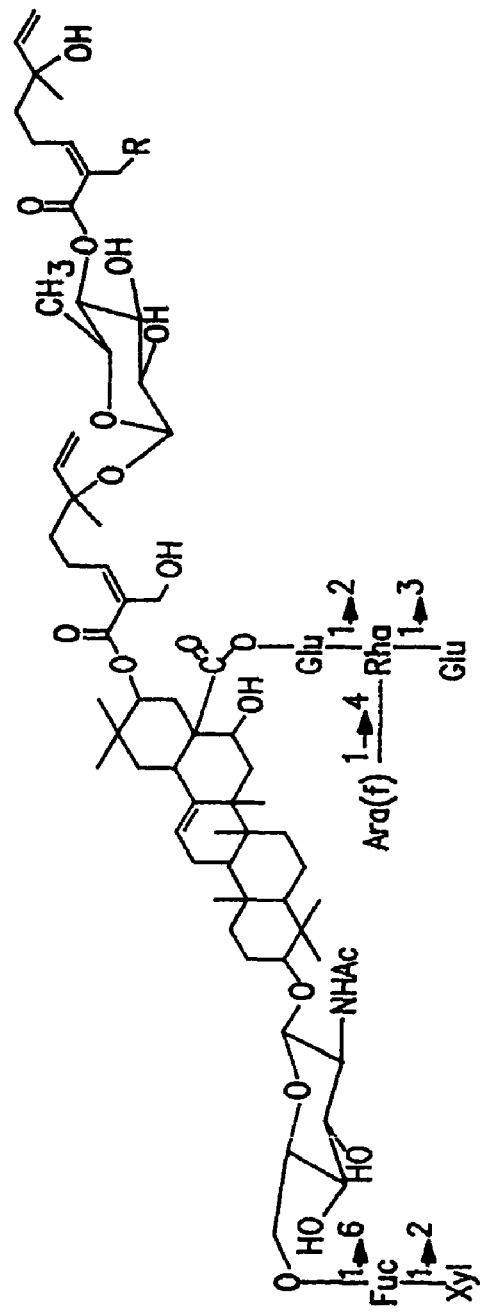
FIG. 5: Structure of Elliptoside A and Elliptoside E (Beutler, 1997).

G1 has the same terpene content and sugars as elliptoside A (see FIG. 5 and Beutler, 1997). However, elliptoside A was found to have a markedly different HPLC retention time (G1—29.09 min. and elliptoside A—26.04 min.), which indicates that the two molecules must differ in some manner such as the specific attachment of their subunits or from the presence of optical isomers or both. A comparison of the proton and carbon NMR spectra of G1 and elliptoside A also show differences in chemical shifts. It is contemplated that the specific rotations of the inner and outer monoterpenes of these compounds may also differ. FIG. 2 structure (14) represents the structure of G1.

1.3. The Structure of B1

Bioactivity data indicates that B1 is much less active than D1 or G1.

1.3.1. Whole Molecule B1 (21)

Figure 3:
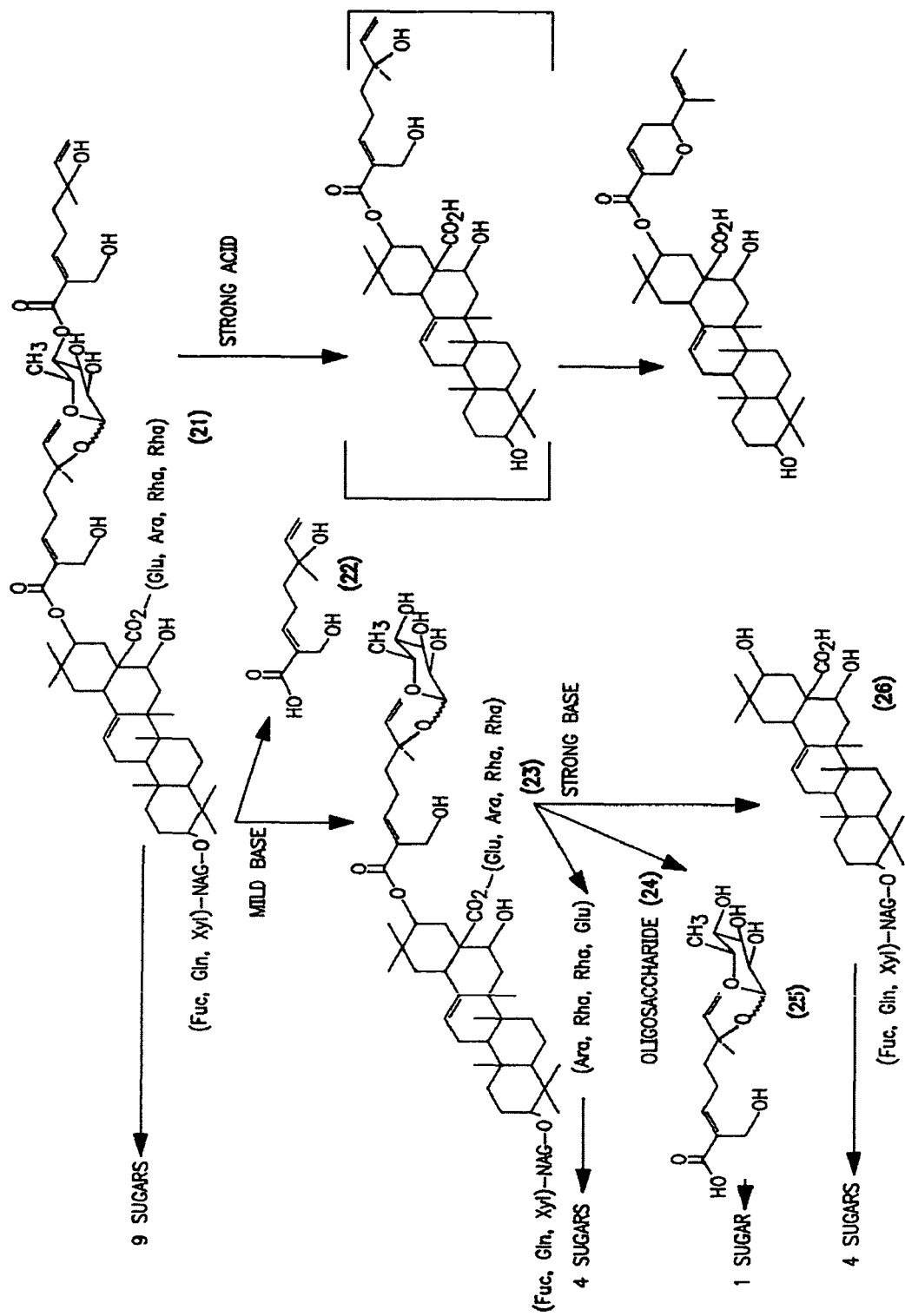
FIG. 3: Depicts compounds from the degradation of compound B1.

The isolation of B1 was accomplished by plant extraction and C-18 flash chromatography followed by C-18 prep and semi-prep chromatography. The NMR of B1 indicates the same triterpene/monoterpene/quinovose/monoterpene structure as has been seen throughout this saponin family. The NMR also indicates the presence of four deoxy sugars and one N-acetyl group, which indicates that this molecule must differ from D1 in its sugar portions. See Table 11 for specific $^{13}$C-NMR assignments under (21). This molecule was degraded as shown in FIG. 3.

1.3.2. Sugar Analysis of B1

NMR data indicate the presence of more than one copy of one of the 6-deoxy methyl sugars (i.e. fucose, rhamnose, 6-deoxyglucose). Sugar analysis of the total molecule after hydrolysis (2N HCl at 100° C. for 2 hours) indicates that nine sugars are present: one molecule each of fucose, arabinose, xylose, quinovose, and glucosamine and two molecules of glucose and rhamnose. Glucosamine, the remnant of an N-acetyl glucosamine, is present in the original molecule. The structure of B 1 is depicted in FIG. 3, structure (21).

1.3.3. Mild Saponification of B1

When B1 was treated with 0.5 N NH$_4$OH at room temperature for even a few minutes there is complete conversion into a more polar compound, the mild saponification product, and a monoterpene.

1.3.3.a. Monoterpene The molecular weight and NMR of this material indicates that it has the same structure as the monoterpene from D1, depicted in FIG. 2 by the structure labeled (5). This is depicted in FIG. 38 by the structure labeled (22).

1.3.3.b. Triterpene Monoterpene Oligosaccharide The NMR of this compound indicates that it contains acacic acid, one monoterpene and several monosaccharides. This is depicted in FIG. 3 by the structure labeled (23).

1.3.4. More Aggressive Saponification of the Triterpene Monoterpene Oligosaccharide A more aggressive saponification (0.3N NaOH at 60° C. for 1 hour) of the mild saponification product allowed the isolation of three molecules in a similar manner as before in D1 and G1. Sugar analyses and NMR data were obtained for each.

1.3.4.a. Oligosaccharide contained glucose, arabinose and two molecules of rhamnose. This is depicted in FIG. 3 by the structure labeled (24).

1.3.4.b. Monoterpene Glycoside contained 6-deoxyglucose and a monoterpene. This is depicted in FIG. 3 by the structure labeled (25).

1.3.4.c. Triterpene Glycoside contained acacic acid with a tetrasaccharide attached at the C-3 position. The tetrasaccharide is composed of one molecule each of N-acetyl glucosamine, fucose, glucose, and xylose. This is depicted in FIG. 3 by the structure labeled (26).

Example 2

Preparation of Avicin-Coated Stent

The stent of the present invention may be prepared in any suitable manner such that a therapeutically amount of an avicin is placed on the stent, within the stent, or both. A stent may be selected for such coating, for example a stent designed such that it imparts minimal injury to the vessel. In specific embodiments, an additional material may be added to the stent to improve its functionality, such as gold, silicon carbide, or polymers, such as polylactic acid and fibrin. In another specific embodiment, a therapeutic composition other than an avicin is applied to the stent, such as an anti-inflammatory agent; an anti-proliferative agent, such as rapamycin or Taxol; an anti-clotting agent, such as heparin, and so forth. In one aspect of the invention, more than one coat of any of the materials placed onto the stent is applied.

The coating of the stent may be performed in any suitable manner. In specific embodiments, the coating is performed as described in U.S. Pat. No. 6,120,847. The method is for coating a stent with a polymeric material having a therapeutic substance dispersed therein for timed release of the therapeutic substance when said stent is implanted such that the coating is generally free of polymeric strands, polymeric particles or other polymeric surface aberrations. A stent having a surface generally defined by a plurality of interconnected struts with open interstitial spaces therebetween, for example, is provided. At least a portion of the surface of the stent is coated with a polymeric material in a solvent carrier, followed by drying the polymeric material by evaporating at least a portion of the solvent carrier to form a dried polymeric coating. When some of the dried polymeric material extends across said interstitial spaces, the dried polymeric coating is contacted with a vaporized solvent, thereby eliminating the polymeric material extending across the interstitial spaces.

Another method in accordance with U.S. Pat. No. 6,153,252 may also be used, where the stent is contacted with a liquid coating solution containing a film forming biocompatible polymer comprising the avicin under conditions that allow the stent to be coated while maintaining a fluid flow through said passages. By doing so, there is prevention of blockage of the passages. Specifically, fluid movement is created by contacting a mandrel with the inner surface of the stent and moving the mandrel relative to the stent to prevent bridges from forming in the passages.

Example 3

Delivery of Avicin-Coated Stent to a Patient

Although the stents of the present invention may be utilized for any application wherein a stent would be beneficial and wherein an avicin would provide a physiological and/or therapeutic effect, in a particular embodiment the avicin-coated stent is utilized in a coronary vessel, such as a coronary artery.

An avicin-coated stent is obtained, such as is described in Example 27. The individual for receipt of the stent may require the stent following another coronary artery procedure, such as angioplasty. Any suitable method for placement of the stent may be employed, although in specific embodiments, the coronary stent is collapsed to a small diameter and placed over a balloon catheter. Upon moving it into the area of the blockage, the balloon is inflated, the stent expands, and then locks in place to form a scaffold that holds the artery open. The stent may be permanent or it may be temporary. Following placement of the stent, the individual may receive additional therapy, such as additional coronary artery disease therapy, (including aspirin; other drugs, such as nitroglycerin, beta blockers, calcium channel blockers, etc.; lifestyle changes, such as diet modification and exercise; and so forth), additional restenosis therapy (such as rapamycin or Taxol), or both.

All of the composition and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the claims.

REFERENCES

The following references, to the extent that they provide exemplary procedural or other details supplementary to those set forth herein, are specifically incorporated herein by reference.

Patents and Patent Applications

U.S. Pat. No. 5,733,327
U.S. Pat. No. 5,797,887
U.S. Pat. No. 5,843,172
U.S. Pat. No. 5,891,108
U.S. Pat. No. 5,972,027
U.S. Pat. No. 6,120,847
U.S. Pat. No. 6,153,252
U.S. Pat. No. 6,206,915
U.S. Pat. No. 6,444,233
U.S. Pat. No. 6,656,162
U.S. Patent Application Ser. No. 60/099,066, filed Sep. 3, 1998
U.S. Patent Application Ser. No. 60/085,997, filed May 19, 1998
WO 2004/012676
WO 00/10552

Publications

Aerts et al., *Plant J.*, 5:635-643, 1994.
Agrawal, "NMR spectroscopy in the structural elucidation of oligosaccharides and glycosides," Phytochemistry, 31:3307-3330, 1992.
Aird, Hamill, Rhodes, "Cytogenetic analysis of hairy root cultures from a number of species transformed by *Agrobacterium rhizogenes*," Plant Cell Tissue Organ Cult., 15:47-57; 1988.
Akiyama et al., *J. Biol. Chem.*, 262:5592-5595, 1987.
Allen et al., "Leguminosae, A source book of characteristics uses and nodulation," The University of Wisconsin Press, Madison, Wis., 1981.
Armitage, In: Statistical *Methods in Medical Research*, Wiley and Sons, New York, N.Y., p 205, 1971.
Arnon, R., et al., *Proc. Natl. Acad. Sci.* (USA) 77:6769-6772 1980.
Baba, Hanada, Hashimoto, "The study of ultraviolet B-induced apoptosis in cultured mouse keratinocytes and in mouse skin," *J. Dermatol. Sci.*, 12:18-23, 1996.
Baxter, Price, Fenwick, "Sapogenin structure: analysis of the $^{13}$C- and $^{1}$H-NMR spectra of soyasapogenol b," *J. Nat. Prod.*, 53:298-302, 1990.
Bellacosa, Feo, Godwin, Bell, Cheng, et al., *Int. J. Cancer*, 64:280-285, 1995.
Berton, Mitchell, Fischer, Locniskar, "Epidermal proliferation but not the quantity of DNA photodamage is correlated with UV-induced mouse skin carcinogenesis," *Invest. Dermatol.*, 109:340-347, 1997.
Beutler, Kashman, Pannell, Cardellina, Alexander, Balaschak, Prather, Shoemaker, Boyd, *Bioorganic and Medicinal Chemistry*, 5:1509-1517, (1997).

Boll and von Philipshorn, "NMR studies and the absolute configuration of *Solanum* alkaloids (spiroaminoketalalkaloids), *Acta Chem. Scand.,* 19:1365-1370, 1965.

Brinkmann et al., *Proc. Natl. Acad. Sci.,* USA, 88(19):8616-8620, 1991.

Burchell et al., *J. Immunol.,* 131(1):508-513, 1983.

Campbell, in Monoclonal Antibody Technology, Laboratory Techniques in Biochemistry and Molecular Biology Vol. 13, Burden and Von Knippenberg, Eds. pp. 75-83, Amsterdam, Elseview, 1984.

Capaldi et al., *Biochem. Biophys. Res. Comm.,* 76:425, 1977.

Capon and Thacker, "The nuclear magnetic resonance spectra of some aldofuranosides and acyclic aldose acetals," *Proc. Chem. Soc. Lond.,* 369, 1964.

Chatterjee, Agarwal, Muhtar, "Ultraviolet B radiation-induced DNA lesions in mouse epidermis," *Biochem. Biophys. Res. Commun.,* 229:590-595, 1996.

Cheatham et al., *Proc. Natl. Acad. Sci.,* 92:11696-11700, 1995.

Cheeke, *Can. J. Animal Sci.,* 51:621-632, 1971.

Chen and Snyder, "Diosgenin-bearing, molluscicidal saponins from *Allium vineale*: an NMR approach for the structural assignment of oligosaccharide units," *J. Org. Chem.,* 54:3679-3689, 1989.

Chen and Snyder, "Molluscicidal saponions form *Allium vineale*," *Tetrahedron Lett.,* 28:5603-5606, 1987.

Cho, Widholm, Tanaka, Nakanishi, Murooka, "*Agrobacterium rhizogenes*-mediated transformation and regeneration of the legume *Astragalus sinicus* (Chinese milk vetch)," *Plant Science,* 138:53-65; 1998.

Chou and Blenis, *Cell,* 85:573-583, 1996.

Christey, "Transgenic crop plants using *Agrobacterium rhizogenes*-mediated transformation," Doran, P. M., (ed.) *Hairy roots: Culture and applications*, Harwood, Amsterdam, 99-111, 1997.

Colcher et al., *Cancer Res.,* 47:1185 and 4218, 1987.

Coliart, Baeuerle, Vassalli, *Mol. Cell. Biol.,* 10:1498-1506, 1990.

Creelman et al., *Proc. Natl. Acad. Sci. USA,* 89:4938-4941, 1992.

Davis & Preston *Analytical Biochemistry,* 116(2):402-407, 1981.

Davis, Sinensky, Junker, *Pharmac. Ther.,* 43:221-36, 1989.

Defago, *Ber. Schweiz. Bot. Ges.,* 87:79-132, 1977.

Dillman et al., *Antibody Immunocon. Radiopharm.,* 1:65-77, 1988.

Doll, R. et al., *Lancet* 1:793, 1962.

Enari, Hug, Nagata, *Nature,* 375:78-81, 1995.

Folkman, Haudenschild, Zetter, *Proc. Natl. Acad. Sci.,* 76:5217-5221, 1979.

Franceschi et al., *Proc. Natl. Acad. Sci. USA,* 88:6745-6749, 1991.

Frechet, Christ, du Sorbier, Fischer, Vuilhorgne, "Four triterpenoid saponins from dried roots of *Gypsophila* species," *Phytochemistry,* 30:927-931, 1991.

Gallo et al., *Circulation,* 99:2164-2170, 1999.

Gamborg, Miller, Ojima, "Nutrient requirements of suspension cultures of soybean root cells," *Exp. Cell Res.,* 50:151-158; 1968.

Gariboldi, Verotta, Gabetta, "Saponins from *Crossopteryx febrifuga, Phytochemistry,* 29:2629-2635, 1990.

Gefter et al., *Somatic Cell Genet.,* 3: 231-236, 1977.

Ghose et al., *CRC Critical Reviews in Therapeutic Drug Carrier Systems,* 3:262-359, 1987.

Ghose, et al., *Meth. Enzymology,* 93:280-333, 1983.

Goding, 1986, In: *Monoclonal Antibodies: Principles and Practice,* 2d ed., Academic Press, Orlando, Fla., pp. 60-61, and 71-74, 1986.

Grant, Dommisse, Christey, Conner, "Gene transfer to plants using *Agrobacterium,*" In: Murray, D. R., (ed.) *Advanced methods in plant breeding and biotechnology*, CAB International, Wallingford, 1991:50-73.

Gundalch et al., *Proc. Natl. Acad. Sci. USA,* 89:2389-2393, 1992.

Hamburger, Slacanin, Hostettmann, Dyatmiko, Sutarjadi, "Acetylated saponins with molluscicidal activity from *Sapindus rarak*: unambiguous structure determination by proton nuclear magnetic resonance and quantitative analysis," *Phytochem. Anal.,* 3:231-237, 1992.

Hanausek et al. *Proc. Natl. Acad. Sci. USA,* 98(20:11551-11556, 2001.

Hansen, Nielsen, Berg, *J. Immunological Methods,* 119:203-210, 1989.

Haridas et al. *Proc. Natl. Acad. Sci. USA,* 98(20):11557-11562, 2001a.

Haridas et al. *Proc. Natl. Acad. Sci. USA* 98(10):5821-5826, 2001b.

Haridas et al. *J. Clin. Invest.* 113(1):65-73, 2004.

Harlow and Lane, Antibodies: A Laboratory manual, Cold Spring Harbor Laboratory, 1988.

Harwood, Chandler, Pellarin, Bangerter, Wilkins, Long, Cosgrove, Malinow, Marzetta, Pettini, Savoy, Mayne, "Pharmacologic consequences of cholesterol absorption inhibition: alteration in cholesterol metabolism and reduction in plasma cholesterol concentration induced by the synthetic saponin β-tigogenin cellobioside (CP-88,818; tiqueside), *J. Lipid. Res.* 34:377-395, 1993.

Hassanain, Dai, Gupta, *Anal. Biochem.,* 213:162-167, 1993.

Hostettmann et al., "Chemistry and pharmacology of natural products," In Saponins, Cambridge University Press, pp. 1-548, 1995.

Hu, Alfermann, "Diterpenoid production in hairy root cultures of *Salvia miltiorrhiza*," *Phytochemistry,* 32(3):699-703; 1993.

Huang et al., *Zhongueo Yaoii Xuebao*, Chemical abstract No. 98100885, 3:286-288, 1982.

Ikeda, Fujiwara, Kinjo, Nohara, Ida, Shoji, Shingu, Isobe, Kajimoto, *Bull. Chem. Soc. Jpn.,* 68:3483-3490 (1995).

Inoue, H., et al., *Chem. Pharm. Bull.* 6) 2:897-901, 1986.

Jansakul, Baumann, Kenne, Samuelsson, "Ardisiacrispin A and B, two utero-contracting saponins from *Ardisia crispa*," *Planta Medica,* 53:405-409, 1987.

Jiang, Massiot, Lavaud, et al., "Triterpenoid glycosides from the bark of *Mimosa tenuiflora, Phytochemistry,* 30:2357-2360, 1991.

Jung, Kwak, Kim, Lee, Choi, Lin, "Improvement of the catharanthine productivity in hairy root cultures of *Catharanthus roseus* by using monosaccharides as a carbon source," *Biotech. Lett.,* 14:695-700; 1992.

Kamel, Ohtani, Kurokawa, et al., "Studies on *Balanites aegyptiaca* fruits, an antidiabetic Egyptian folk medicine," *Chem. Pharm. Bull.,* 39:1229-1233, 1991.

Kasiwada et al., *J. Org. Chem.,* 57:6946-6953, 1992.

Kelly and Tsai, "Effect of pectin, gum arabic and agar on cholesterol absorption, synthesis and turnover in rats," *J. Nutr.,* 108:630-639, 1978.

Kennedy, Wagner, Conzen, Jordan, Bellacosa, Tsichlis, Nissam, *Genes and Dev.,* 11:701-713, 1997.

Kimura et al., *Immunogenetics,* 11:373-381, 1983.

Kinjo, Araki, Fukui, Higuchi, Ikeda, Nohara, Ida, Takemoto, Miyakoshi, Shoji, *Chem. Pharm. Bull.* 40(12):3269-3273 (1992).

Kizu and Tomimori, "Studies on the constituents of *Clematis* species. V. On the saponins of the root of *Clematis chinensis* OSBECK," *Chem. Pharm. Bull.*, 30:3340-3346, 1982.

Kohler and Milstein, *Eur. J. Immunol.*, 6:511-519, 1976.

Kohler and Milstein, *Nature*, 256:495-497, 1975.

Kojima and Ogura, "Configurational studies on hydroxy groups at C-2, 3 and 23 or 24 of oleanene and ursene-type triterpenes by NMR spectroscopy," *Phytochemistry*, 28:1703-1710, 1989.

Kong et al., *Phytochemistry*, 33:427-430, 1993.

Konoshima and Sawada, *Chem. Pharm. Bull.*, 30:2747-2760, 1982.

Kutney, "Nuclear magnetic resonance (N.M.R.) study in the steroidal sapogenin series. Stereochemistry of the spiro ketal system," *Steroids*, 2:225-235, 1963.

Lanza, et al., *Circulation*, 106:2842-2847, 2002.

Lemieux, Kullnig, Bernstein, Schneider, "Configurational effects on the proton magnetic resonance spectra of six-membered ring compounds," *J. Am. Chem. Soc.*, 80:6098-6105, 1958.

Lister, P. R., P. Holford, T. Haigh, and D. A. Morrison. *Acacia in Australia: Ethnobotany and potential food crop.* p. 228-236. In: J. Janick (ed.), *Progress in new crops*. ASHS Press, Alexandria, Va., 1996.

Lloyd, McCown, "Commercially feasible micropropagation of mountain laurel, *Kalmia latifolia* by use of shoot tip culture," *Comb. Proc. Intl. Plant Prop. Soc.*, 30:421-427; 1981.

Mackness, Durrington, Converse, Skinner (Eds.), *In: Lipoprotein Analysis: A Practical Approach*, Oxford University Press, Oxford, p 1, 1992.

Mahato, Pal, Nandy, *Tetrahedron*, 48:6717-6728 (1992).

Manabe et al., *J. Lab. Clin. Med.*, 104(3):445-454, 1984.

Martin et al., *J. Exp. Med.*, 182:1545-1556, 1995.

Martin, Reueelingsperger, McGahon, Rader, van Schie, Laface, Green, *J. Exp. Med.*, 182:1545-1556, 1995.

Massiot, Lavaud, Besson, Le Men-Olivier, van Binst, "Saponins from aerial parts of alfalfa (*Medicago sativa*)," *J. Agric. Food Chem.*, 39:78-82, 1991b.

Massiot, Lavaud, Delaude, van Binst, Miller, Fales, "Saponins from *Tridesmostemon claessenssi*," *Phytochemistry*, 29:3291-3298, 1990.

Massiot, Lavaud, Guillaume, Le Men-Olivier, van Binst, "Identification and sequencing of sugars in saponins using 2D $^1$H NMR spectroscopy," *J. Chem. Soc., Chem. Commun.*, 1485-1487, 1986.

Massiot, Lavaud, Le Men-Olivier, van Binst, Miller, Fales, "Structural elucidation of alfalfa root saponins by mass spectrometry and nuclear magnetic resonance analysis," *J. Chem. Soc., Perkin Trans.*, 1:3071-3079, 1988.

Massiot, Lavaud, Nuzillard, "Révision des structures des chrysantéllines par résonance magnétique nucléaire," *Bull. Soc. Chim. Fr.*, 127:100-107, 1991a.

Miotti et al., *Cancer Res.*, 65:826, 1985.

Miyamoto, Togawa, Higuchi, Komori, Sasaki, "Six newly identified biologically active triterpenoid glycoside sulphates from the sea cucumber," *Cucumaria echinata. Annalen*, 453-460, 1990.

Monk, "Variegation in epigenetic inheritance", *TIG*, 6:110-114, 1990.

Mujoo, Maneval, Anderson, Gutterman, *Oncogene*, 12:1617-1623, 1996.

Mujoo et al. *Cancer Res.*, 61:5486-5490, 2001.

Murashige, Skoog, "A revised medium for rapid growth and bioassay of tobacco tissue culture," *Physiol. Plant.*, 15:473-482; 1962.

Murashige, T and Skoog, F. "A revised medium for rapid growth and bio-assays with tobacco tissue cultures," *Physiologia Plantarum* 15: 473-497, 1962.

Nabel and Baltimore, *Nature* 326:711-713, 1987.

Nagamoto et al., *Planta Medica.*, 54:305-307, 1988.

Nagao, Hachiyama, Oka, Yamauchi, "Studies on the constituents of *Aster tataricus* L. f. II. Structures of aster saponins isolated from the root," *Chem. Pharm. Bull.*, 37:1977-1983, 1989.

Nelson, Futscher, Kinsella, Wymer, Bowden, "Detection of mutant Ha-ras genes in chemically initiated mouse skin epidermis before the development of benign tumors," *Proc. Natl. Acad. Sci. USA*, (14):6398-6402, 1992.

Nishino, Manabe, Enoki, Nagata, Tsushida, Hamaya, "The structure of the tetrasaccharide unit of camellidins, saponins, possessing antifungal activity," *J. Chem. Soc., Chem. Commun.*, 720-723, 1986.

Nitsch, Nitsch, "Haploid plants from pollen grains," *Science*, 163:85-87, 1969.

O'Reilly, Boehm, Shing, Fukai, Vasios, Lane, Flynn, Birkhead, Olsen, Folkman, *Cell*, 88:277-285, 1997.

Oakenfull et al., *Atherosclerosis*, 48:301 (1983).

Ohkawa, Kamada, Sudo, Harada, "Effects of gibberellic acid on hairy root growth in *Datura innoxia*," *J. Plant Physiol.*, 134:633-636; 1989.

Okabe, Nagao, Hachiyama, Yamauchi, "Studies on the constituents of *Luffa operculata* COGN. II. Isolation and structure elucidation of saponins in the herb," *Chem. Pharm. Bull.*, 37:895-900, 1989.

Okada, Koyama, Takahashi, Okuyama, Shibata, *Planta Med.* 40:185-192, (1980).

Okada, Sakuma, Fukui, Hazeki, Ui, *J. Bio. Chem.*, 269:3563-3567, 1994.

Pallavicini, *In: Techniques in Cell Cycle Analysis*, Gray and Parzynkiewicz (Eds.), Humana Press Inc., Clifton, N.J., pp. 139, 1987.

Pant, Panwar, Negi, Rawat, Morris, Thompson, "Structure elucidation of a spirostanol glycoside from *Asparagus officinalis* fruits by concerted use of two-dimensional NMR techniques," *Mag. Reson. Chem.*, 26:911-918, 1988.

Penders, Delaude, Pepermans, van Binst, "Identification and sequencing of sugars in an acetylated saponin of *Blighia welwitschii* by N.M.R. spectroscopy," *Carbohyd. Res.*, 190:109-120, 1989.

Pietenpol et al., *Cancer Res.*, 55:1206-1210, 1995.

Pieterez et al., *Antibody Immunoconj. Radiopharm.*, 1:79-103, 35, 1988.

Pisha et al., *Nature Medicine*, 1:1046-1051, 1995.

Polyak et al., *Genes Dev.*, 8:9-22, 1994.

Potterat, Hostettmann, Stoeckli-Evans, Saadou, "Saponins with an unusual secoursene skeleton from *Sesamum alatum* THONN., *Helv. Chim. Acta*, 75:833-841, 1992.

Prehn, "Regeneration versus neoplastic growth," *Carcinogenesis*, 18(8):1439-1444, 1997.

Puri, Wong, Puri, "Solasodine and diosgenin: $^1$H and $^{13}$C assignments by two-dimensional NMR spectroscopy," *Mag. Res. Chem.*, 31:278-282, 1993.

Reeves, Nielson, Fahey, *Am. Inst. Nutr.*, 1939, 1993.

Reisfeld et al., *Melanoma Antigens and Antibodies*, p. 317, 1982.

Reznicek, Jurenitsch, Kubelka, Michl, Korhammer, Haslinger, "Isolierung und Struktur der vier Hauptsaponine aus *Solidago gigantea* var. *serotina*," *Annalen*, 989-994, 1990.

Reznicek, Jurenitsch, Michl, Haslinger, "The first structurally confirmed saponin from *Solidago gigantea*: structure elucidation by modern NMR techniques," *Tetrahedron Lett.*, 30:4097-4100, 1989b.
Reznicek, Jurenitsch, Robien, Kubelka, "Saponins in Cyclamen species: configuration of cyclamiretin C and structure of isocyclamin," *Phytochemistry*, 28:825-828, 1989a.
Rhodes, et al., "Influence of exogenous hormones on the growth and secondary metabolite formation in transformed root cultures," *Plant Cell Tissue Organ Culture*, 38:143-151; 1994.
Rodriguez, Castro, Riguera, "Holothurinosides: new anti-tumour non sulphated triterpenoid glycosides from the sea cucumber *Holothruia forskalii*," *Tetrahedron*, 47:4753-4762, 1991.
Royal I and Park M, *J. Biol. Chem.* 270:27780-27787, 1995.
Sasaki, Udagawa, Ishimaru, Hayashi, Alfermann, Nakanishi, Shimomura, "High forskolin production in hairy roots of *Coleus forskohlii*," *Plant Cell Reports* 17:457-459, 1998.
Sashida, Kawashima, Mimaki, "Novel polyhydroxylated steroidal saponins from *Allium giganteum*," *Chem. Pharm. Bull.*, 39:698-703, 1991.
Schenk, Hilderbrandt, "Medium and techniques for induction and growth of monocotyledonous and dicotyledonous plant cell cultures," *Can. J. Bot.*, 50:199-204; 1972.
Schöpke, Wray, Rzazewska, Hiller, "Bellissaponins $BA_1$ and $BA_2$, acylated saponins from *Bellis perennis*," *Phytochemistry*, 30:627-631, 1991.
Schreiber, Matthias, Muller, Schaffner, *Nucleic Acids Res.*, 17:6419, 1989.
Schuh et al., "Obligatory wounding requirement for tumorigenesis in v-jun transgenic mice," *Nature*, 346:756-760, 1990.
Shao, Kasai, Xu, Tanaka, "Saponins from roots of *Kalopanax septemlobus*. (THUNB.) KOIDZ., Ciqiu: structures of kalopanaxsaponins C, D, E and F," *Chem. Pharm. Bull.*, 37:311-314, 1989.
Shayesteh, Lu, Kuo, Baldocchi, Godfrey, Collins, Pinkel, Powell, Mills, Grey, *Nat. Gent.*, 21:99-102, 1999.
Shepard et al., *J. Clin. Immunol.*, 11:117-127, 1991.
Shirazi, Liu, Trott, "Exposure to ultraviolet B radiation increases the tolerance of mouse skin to daily X-radiation," *Rad. Res.*, 145:768-775, 1996.
Sieweke et al., "Mediation of wound-related rous sarcoma virus tumorigenesis by TGF-β," *Science*, 248:1656-1660, 1990.
Smith, Weathers, Cheetham, "Effects of gibberellic acid on hairy root cultures of *Artemisia annua*: growth and artemisinin production," *In Vitro Cell Dev. Biol.*, 33:75-79; 1997.
Smith, et al., *J. Interventional Cardiology*, 16:475-483, 2003.
Spady, Wollett, Dietschy, *Annu. Rev. Nutr.*, 13:355, 1993.
Steel and Torrie, *In: Principals and Procedures of Statistics*, 2nd Ed., McGraw-Hill, New York, p 383, 1980.
Stevenson et al., *Chem. Immunol.*, 48:126-166, 1990.
Takema, Fujimura, Ohsu, Imokawa, "Unusual wrinkle formation after temporary skin fixation followed by UVB irradiation in hairless mouse skin," *Exp. Dermatol.*, 5:145-149, 1996.
Tewari, Quan, Rourke, Zeng, Beidler, Salvesan, Dixit, "Yama/CPP32 beta, a mammalian homolog of CED-3, is a CrmA-inhibitable protease that cleaves the death substrate poly (ADP-ribose) polymerase," *Cell*, 81:801, 1995.
Thompson et al., *Cancer Epidemiol. Biomarker Prevent.*, 1:597-602, 1992.
Thor et al, *Cancer Res.*, 46:3118, 1986.
Tomas-Barbaren et al., *Planta Medica.*, 54:266-267 (1988).
Tori and Aono, *Ann. Rept. Shionogi Res. Lab.*, 14:136, 1964.
Vaickus et al., *Cancer Invest.*, 9:195-209, 1991.
Vazquez, Quinoa, Riguera, San Martin, Darias, "Santiagoside, the first asterosaponin from an Antarctic starfish (*Neosmilaster georgianus*)," *Tetrahedron*, 48:6739-6746, 1992.
Vlahos and Matter, *FEBS Lett.*, 309:242-248, 1992.
Vlahos, Matter, Hui, Brown, *J. Bio. Chem.*, 269:5241-5248, 1994.
Waltho, Williams, Mahato, Pal, Barna, "Structure elucidation of two triterpenoid tetrasaccharides from *Androsace saxifragifolia*," *J. Chem. Soc., Perkin* 1:1527-1531, 1986.
Wang, He, Ling, Li, "Chemical study of *Astragalus* plant. II. Structures of asemestioside A and B, isolated from *Astragalus ernestii* COMB. *Huaxue Xuebao*, 47:583-587, *Chem. Abstr.*, 1989.
Weng et al., *Proc. Natl. Acad. Sci.*, 92:5744-5748, 1995.
White, *Genes Dev.*, 10:1-15, 1996.
Whitman M, Kaplan D. R., Schatthausen B, Cantley L. C. and Roberts, T. M. *Nature*, 315: 239-242, 1985.
Willker and Leibfritz, "Complete assignment and conformational studies of tomatine and tomatidine," *Mag. Res. Chem.*, 30:645-650, 1992.
Wyllie, *Anticancer Res.*, 5:131-136, 1985.
Wysokinska, Chmiel, "Transformed root cultures for biotechnology," *Acta Biotechnol.*, 17:131-159; 1997.
Yang et al., *Anticancer Res.*, 15:2479-2488, 1995.
Yoshikawa, Shimono, Arihara, "Antisweet substances, jujubasaponins I-III from *Zizyphus jujuba*, Revised structure of ziziphin," *Tetrahedron Lett.*, 32:7059-7062, 1991.
Yoshikawa, Suzaki, Tanaka, Arihara, Nigam, *J. Nat. Prod.*, 60:1269-1274 (1997).
Youn, Park, Chung, Lee, *Photodermatol Photoimmunol. Photomed.*, 13:109-114, 1997.
Yukimune et al., *Nature Biotech.*, 14:1129-1132, 1996.
Zobel, "Study-state control and investigation of root system morphology," In: Torrey J. G., Winship, L. J. (eds.) *Applications of continuous and steady-state methods to root biology*, Kluwer, Amsterdam, 165-182, 1989.

What is claimed is:

1. A stent comprising an avicin.

2. The stent of claim 1, wherein said avicin is Avicin D, Avicin G, Avicin B, or a mixture thereof.

3. The stent of claim 1, wherein the avicin is further defined as a composition comprising a triterpene moiety attached to a monoterpene moiety having the molecular formula:

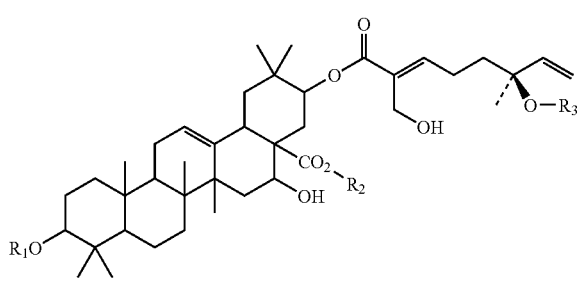

or a pharmaceutical formulation thereof, wherein
a) $R_1$ and $R_2$ are selected from the group consisting of hydrogen, C1-C5 alkyl, and an oligosaccharide;
b) $R_3$ is selected from the group consisting of hydrogen, hydroxyl, C1-C5 alkyl, C1-C5 alkylene, C1-C5 alkyl carbonyl, a sugar, and a monoterpene group; and c) the formula further comprises $R_4$, wherein $R_4$ is selected from the group consisting of hydrogen, hydroxyl, C1-C5 alkyl, C1-C5 alkylene, C1-C5 alkyl carbonyl, a sugar, C1-C5 alkyl ester, and a monoterpene group, and wherein $R_4$ may be attached to the triterpene moiety or the monoterpene moiety.

4. The stent of claim 3, wherein $R_3$ is a sugar.

5. The stent of claim 4, wherein the sugar is selected from the group consisting of glucose, fucose, rhamnose, arabinose, xylose, quinovose, maltose, glucuronic acid, ribose, N-acetyl glucosamine, and galactose.

6. The stent of claim 5, further comprising a monoterpene moiety attached to the sugar.

7. The stent of claim 6, wherein $R_3$ has the following formula

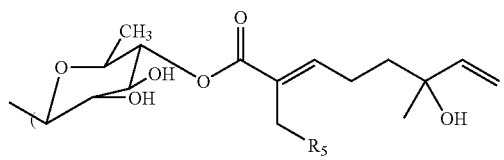

wherein R5 is selected from the group consisting of hydrogen, hydroxyl, C1-C5 alkyl, C1-C5 alkylene, C1-C5 alkyl carbonyl, a sugar, C1-C5 alkyl ester, and a monoterpene group.

8. The stent of claim 7, wherein $R_5$ is a hydrogen or a hydroxyl.

9. The stent of claim 3, wherein $R_1$ and $R_2$ each comprise an oligosaccharide.

10. The stent of claim 9, wherein $R_1$ and $R_2$ each comprise a monosaccharide, a disaccharide, a trisaccharide or a tetrasaccharide.

11. The stent of claim 9, wherein $R_1$ and $R_2$ each comprise an oligosaccharide comprising sugars which are separately and independently selected from the group consisting of glucose, fucose, rhamnose, arabinose, xylose, quinovose, maltose, glucuronic acid, ribose, N-acetyl glucosamine, and galactose.

12. The stent of claim 11, wherein at least one sugar is methylated.

13. The stent of claim 3, wherein $R_4$ is attached to the triterpene moiety through one of the methylene carbons attached to the triterpene moiety.

14. The stent of claim 3, wherein the triterpene moiety is oleanolic acid instead of acacic acid.

15. The stent of claim 1, wherein the avicin composition is further defined as comprising a triterpene glycoside having the molecular formula:

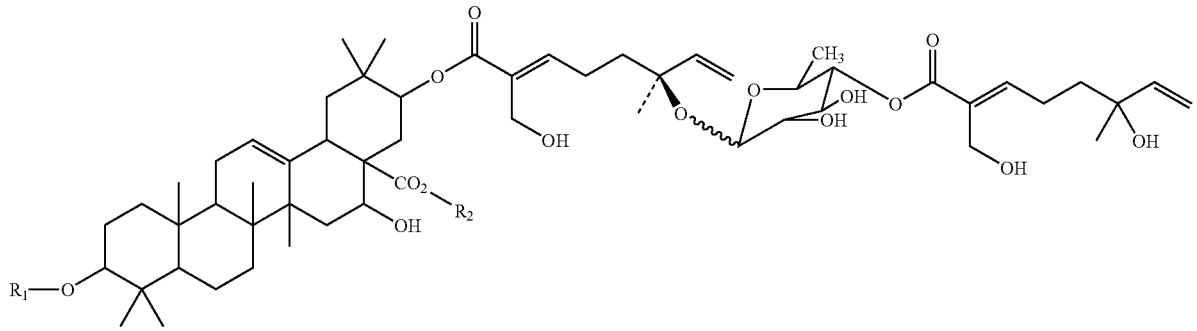

or a pharmaceutical formulation thereof, wherein
a) $R_1$ is an oligosaccharide comprising N-acetyl glucosamine, fucose and xylose; and
b) $R_2$ is an oligosaccharide comprising glucose, arabinose and rhamnose.

16. The stent of claim 15, having the molecular formula:

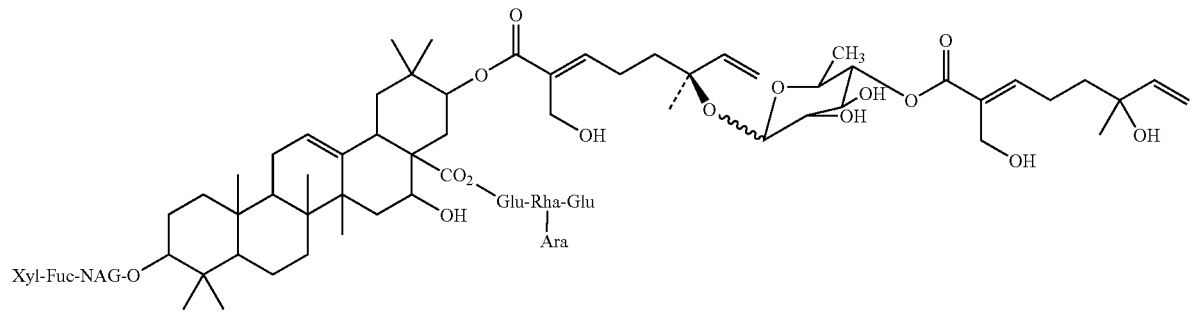

or a pharmaceutical formulation thereof.

17. The stent of claim 1, wherein the avicin is further defined as a triterpene glycoside having the molecular formula:

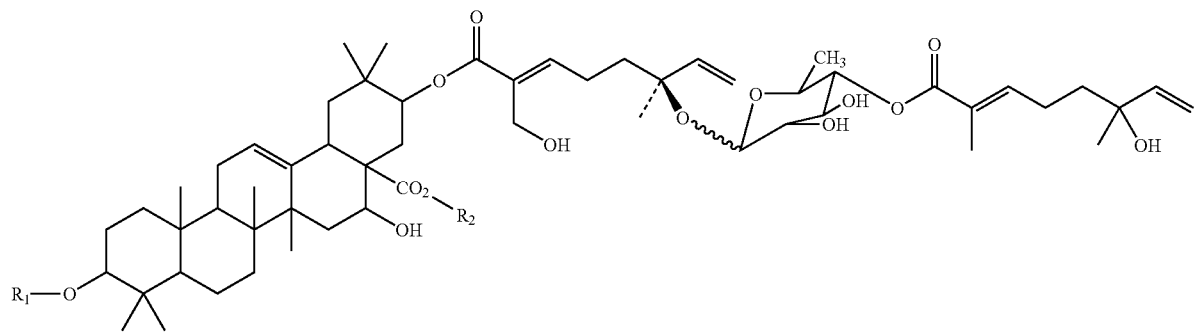

or a pharmaceutical formulation thereof wherein,
a) $R_1$ is an oligosaccharides comprising N-acetyl glucosamine, fucose and xylose; and
b) $R_2$ is an oligosaccharides comprising glucose, arabinose and rhamnose.

18. The stent of claim 17, having the molecular formula:

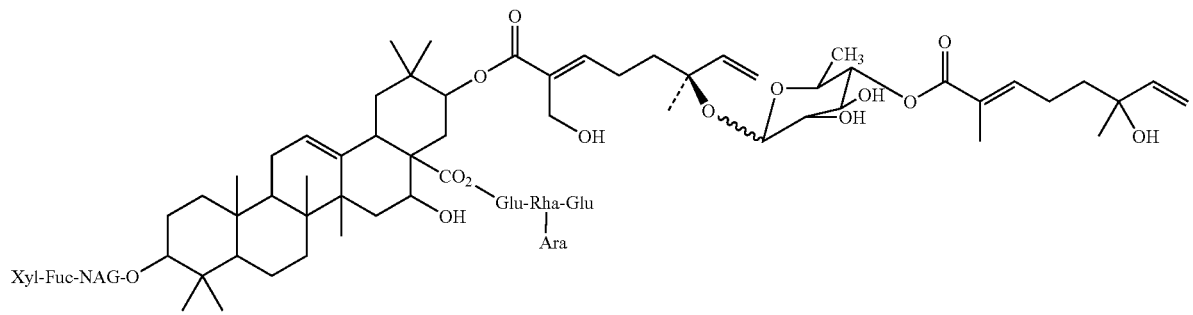

or a pharmaceutical formulation thereof.

19. The stent of claim 1, wherein the avicin is further defined as comprising a triterpene glycoside having the molecular formula:

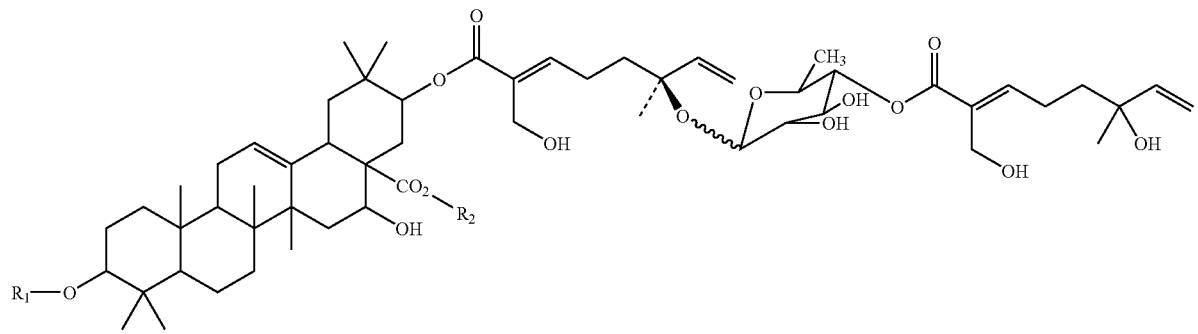

or a pharmaceutical formulation thereof, wherein,
a) $R_1$ is an oligosaccharide comprising N-acetyl glucosamine, glucose, fucose and xylose; and
b) $R_2$ is an oligosaccharide comprising glucose, arabinose and rhamnose.

20. The stent of claim 1, wherein the avicin is further defined as having the molecular formula:

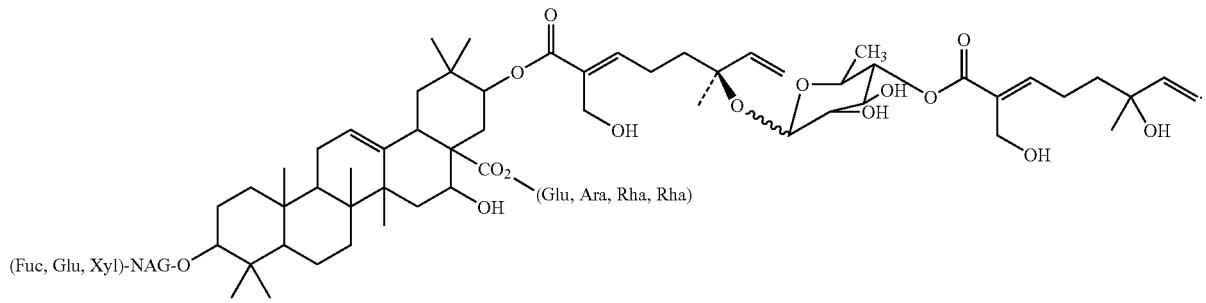

21. The stent of claim 1, wherein the avicin is further defined as comprising a triterpene moiety, an oligosaccharide and three monoterpene units.

22. The stent of claim 21, wherein the triterpene moiety is acacic acid or oleanolic acid.

23. The stent of claim 1, further comprising an additional compound selected from the group consisting of an immunosuppressing agent, an anti-clotting agent, an antibiotic, an anti-inflammatory agent and mixtures thereof.

24. The stent of claim 1, wherein the additional compound is coated on the stent.

25. The stent of claim 1, wherein the stent comprises a corrugated configuration, slotted configuration, a coil configuration, a coil-related configuration, a tubular configuration, a multicellular configuration, or a combination thereof.

26. The stent of claim 1, wherein the stent is comprised of a metal or a polymer.

27. The stent of claim 26, wherein the metal comprises stainless steel, tantalum, nitinol, cobalt-chromium alloy.

28. The stent of claim 26, wherein the polymer is a biodegradable polymer, a synthetic polymer, or both.

29. The stent of claim 28, wherein the biodegradable polymer comprises phosphorylcholine or poly-L-lactic acid.

30. The stent of claim 1, wherein the stent comprises gold or silicon carbide.

\* \* \* \* \*